United States Patent
Kogawa et al.

(10) Patent No.: US 12,115,285 B2
(45) Date of Patent: Oct. 15, 2024

(54) CYLINDRICAL MEMBER FOR IMPLANTATION

(71) Applicant: Toray Industries, Inc., Tokyo (JP)

(72) Inventors: Taisuke Kogawa, Otsu (JP); Masaki Fujita, Otsu (JP); Kazuhiro Tanahashi, Otsu (JP); Satoshi Yamada, Otsu (JP); Nobuaki Tanaka, Otsu (JP); Hiroshi Tsuchikura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 912 days.

(21) Appl. No.: 17/269,502

(22) PCT Filed: Aug. 30, 2019

(86) PCT No.: PCT/JP2019/034060
§ 371 (c)(1),
(2) Date: Feb. 18, 2021

(87) PCT Pub. No.: WO2020/045611
PCT Pub. Date: Mar. 5, 2020

(65) Prior Publication Data
US 2021/0322650 A1 Oct. 21, 2021

(30) Foreign Application Priority Data
Aug. 31, 2018 (JP) .................. 2018-163208

(51) Int. Cl.
| | |
|---|---|
| *A61L 27/58* | (2006.01) |
| *A61L 27/18* | (2006.01) |
| *A61L 27/34* | (2006.01) |
| *A61L 27/50* | (2006.01) |
| *A61L 31/10* | (2006.01) |
| *A61L 31/14* | (2006.01) |
| *C09D 167/04* | (2006.01) |
| *C09D 171/02* | (2006.01) |

(52) U.S. Cl.
CPC .............. *A61L 27/58* (2013.01); *A61L 27/18* (2013.01); *A61L 27/34* (2013.01); *A61L 27/507* (2013.01); *A61L 31/10* (2013.01); *A61L 31/148* (2013.01); *C09D 167/04* (2013.01); *C09D 171/02* (2013.01)

(58) Field of Classification Search
CPC .......... A61L 27/58; A61L 27/18; A61L 27/34; A61L 27/507; A61L 31/10; A61L 31/148; C09D 167/04; C09D 171/02
See application file for complete search history.

(56) References Cited

U.S. PATENT DOCUMENTS

| | | |
|---|---|---|
| 4,826,945 A | 5/1989 | Cohn et al. |
| 2010/0030325 A1* | 2/2010 | Yamaoka ............... C08L 53/00 525/418 |
| 2011/0027336 A1 | 2/2011 | Hossainy et al. |
| 2020/0022799 A1 | 1/2020 | Yamashita et al. |
| 2021/0002432 A1 | 1/2021 | Kogawa et al. |
| 2021/0007838 A1 | 1/2021 | Tanaka et al. |

FOREIGN PATENT DOCUMENTS

| | | | |
|---|---|---|---|
| JP | 01-195862 | 8/1989 | |
| JP | 9-309947 | 12/1997 | |
| JP | 2004-313310 | 11/2004 | |
| JP | 2008-142534 | 6/2008 | |
| JP | 2013-524940 | 6/2013 | |
| WO | 1996/021056 | 7/1996 | |
| WO | 2018/066476 | 4/2018 | |
| WO | WO-2018066476 A1 * | 4/2018 | ............... A61F 2/06 |
| WO | 2018/181918 | 10/2018 | |
| WO | 2019/187569 | 10/2019 | |

OTHER PUBLICATIONS

Messmore, Benjamin et al., Synthesis, Self-Assembly, and Characterization of Supramolecular Polymers from Electroactive Dendron Rodcoil.
Molecules, *Journal of the American Chemical Society 2004*, 126(44): pp. 14452-14458, Oct. 19, 2004.

* cited by examiner

*Primary Examiner* — Snigdha Maewall
(74) *Attorney, Agent, or Firm* — DLA Piper LLP (US)

(57) ABSTRACT

A cylindrical body for an implant is capable of maintaining a high patency rate by achieving a good antithrombogenicity, a low swelling property and a low Young's modulus. A cylindrical body for an implant includes: a cylindrical substrate having an elongation rate in the longitudinal direction, as measured under a tensile load of 20 N, of from 5 to 100%; and a block copolymer composed of a polyalkylene glycol block(s) and a polyhydroxyalkanoic acid block(s); wherein the ratio of the mass of the polyalkylene glycol with respect to the total mass of the block copolymer is 5 to 25%; and a film composed of the block copolymer has a Young's modulus of 200 MPa or less.

8 Claims, 2 Drawing Sheets

CYLINDRICAL MEMBER FOR IMPLANTATION

TECHNICAL FIELD

This disclosure relates to a cylindrical body for an implant.

BACKGROUND

Biodegradable polymers are widely used in medical applications such as, for example, medical coating materials, vascular embolization materials, suture threads and DDS carriers. Medical coating materials to be implanted in the body are retained in the body and, therefore, they need to be nontoxic, and to be eventually degraded and discharged outside the body.

In particular, coating materials that come into contact with blood are required to be biocompatible since their original functions may be lost if they were to induce thrombus formation.

A block copolymer of a polyalkylene glycol and an aliphatic polyester has been reported as a biodegradable polymer having an excellent degradability and antithrombogenicity as described above (JP 9-309947 A and WO 1996/021056 A).

Further, an artificial blood vessel has also been reported in which a copolymer obtained by mixing a component(s) selected from L-lactic acid, D,L-lactic acid, glycolic acid and ε-caprolactone, with a component(s) selected from polyvinyl alcohol and polyethylene glycol, is used as a biodegradable synthetic polymer, and in which such a biodegradable synthetic polymer is coated on a cylindrical article composed of fibers (JP 2004-313310 A).

However, since the block copolymer disclosed in JP 9-309947 A has a high polyalkylene glycol content, the copolymer swells when it comes into contact with blood, leading to the elongation of the resulting artificial blood vessel. Elongation of the artificial blood vessel may lead to a decrease in the inner diameter of the blood vessel, resulting in an increase in the shear rate of blood. Further, in a substrate composed of fibers, a decrease in fiber density causes an increase in the volume of voids into which blood components infiltrate. In any event, the adhesion and aggregation of blood platelets are accelerated, leading to thrombus formation.

The block copolymer disclosed in WO 1996/021056 A has a low polyalkylene glycol content and, thus, the elongation due to swelling does not occur. However, the block copolymer has a high Young's modulus. Due to having a high Young's modulus, the kink resistance of the resulting artificial blood vessel after being coated with the block copolymer is reduced. As a result, the artificial blood vessel fails to conform to the movement of a living body and buckles, leading to the occlusion of the artificial blood vessel.

Thus, even if a conventional block copolymer is used in an artificial blood vessel, there is a possibility that a high patency rate required cannot be maintained because of its high swelling property and high Young's modulus.

Further, in the artificial blood vessel disclosed in JP 2004-313310 A, since polyethylene glycol is mixed in the biodegradable polymer to be coated on the artificial blood vessel, the polyethylene glycol is dissolved at an early stage of implantation, resulting in a failure to maintain the antithrombogenicity. Accordingly, a further improvement is needed to use the artificial blood vessel as an implant capable of maintaining a high patency rate.

Therefore, it could be helpful to provide a cylindrical body for an implant capable of maintaining a high patency rate by achieving a good antithrombogenicity, a low swelling property and a low Young's modulus.

SUMMARY

We thus provide the following (1) to (9):

(1) A cylindrical body for an implant, including:
   a cylindrical substrate having an elongation rate in the longitudinal direction, as measured under a tensile load of 20 N, of from 5 to 100%; and
   a block copolymer composed of a polyalkylene glycol block(s) and a polyhydroxyalkanoic acid block(s);
   wherein the ratio of the total mass of the alkylene glycol residue(s) with respect to the total mass of the block copolymer is from 5 to 25%; and wherein the block copolymer has a Young's modulus, as measured in the form of a film, of 200 MPa or less.

(2) The cylindrical body according to (1), wherein the polyhydroxyalkanoic acid block includes a residue selected from the group consisting of lactic acid, glycolic acid and caprolactone residues.

(3) The cylindrical body according to (2),
   wherein the polyhydroxyalkanoic acid block includes a caprolactone residue(s); and
   wherein the ratio of the total mass of the caprolactone residue(s) with respect to the total mass of the block copolymer is from 15 to 80%.

(4) The cylindrical body according to (2) or (3),
   wherein the polyhydroxyalkanoic acid block includes a glycolic acid residue(s); and
   wherein the ratio of the total mass of the glycolic acid residue(s) with respect to the total mass of the block copolymer is from 10% or less.

(5) The cylindrical body according to any one of (1) to (4), wherein the cylindrical substrate satisfies Formula (1):

$$(L2-L1)/L1 \geq 0.1 \quad (1)$$

wherein L1 represents a gauge length when the cylindrical substrate is compressed in the longitudinal direction thereof at a stress of 0.01 cN/dtex, wherein the gauge length is the distance between gauge lines drawn on the outer periphery of the cylindrical substrate, spaced apart by a distance 5 times the maximum value of the outer diameter of the cylindrical substrate as measured without applying a stress to the cylindrical substrate; and
   wherein L2 represents the gauge length when the cylindrical substrate is elongated in the longitudinal direction thereof at a stress of 0.01 cN/dtex.

(6) The cylindrical body according to any one of (1) to (5), wherein the cylindrical substrate satisfies Formula (2):

$$0.03 \leq (a-b)/a < 0.2 \quad (2)$$

wherein a represents the outer diameter of the cylindrical substrate as measured when the cylindrical substrate is compressed in the longitudinal direction thereof at a stress of 0.01 cN/dtex; and
   wherein b represents the outer diameter of the cylindrical substrate as measured when the cylindrical substrate is elongated in the longitudinal direction thereof at a stress of 0.01 cN/dtex.

(7) The cylindrical body according to any one of (1) to (6), wherein the surface roughness of the inner surface of the cylindrical substrate is 100 μm or less.

(8) An artificial blood vessel including the cylindrical body according to any one of (1) to (7).

(9) A stent graft including the cylindrical body according to any one of (1) to (7).

Our cylindrical body for an implant is capable of maintaining a high patency rate hitherto unachievable by forming the cylindrical body by coating a block copolymer which is composed of a polyalkylene glycol block(s) and a polyhydroxyalkanoic acid block(s) and whose monomer weight ratio is controlled, on a cylindrical substrate having a specific elongation rate. In particular, the cylindrical body for an implant can be suitably used as a material for a medical device used for cardiovascular implantation.

DETAILED DESCRIPTION

The cylindrical body for an implant is characterized by including:
a cylindrical substrate having an elongation rate in the longitudinal direction, as measured under a tensile load of 20 N, of 5 to 100%; and a block copolymer composed of a polyalkylene glycol block(s) and a polyhydroxyalkanoic acid block(s);
wherein the ratio of the mass of the polyalkylene glycol with respect to the total mass of the block copolymer is from 5 to 25%; and
a film composed of the block copolymer has a Young's modulus of 200 MPa or less.

When the cylindrical substrate has an elongation rate in the longitudinal direction, as measured under a tensile load of 20 N, of 5% or more, the cylindrical substrate more easily conforms to the movement of a living body, when implanted in the body. When the cylindrical substrate has an elongation rate of 100% or less, the substrate can be prevented from meandering during surgery, and can be more easily implanted at an intended site. Based on the above, the cylindrical substrate preferably has an elongation rate in the longitudinal direction, as measured under a tensile load of 20 N, of 5% to 100%, more preferably 7% to 75%, and still more preferably 10% to 50%. The elongation rate in the longitudinal direction, as measured under a tensile load of 20 N, can be measured in accordance with Measurement Example 4 to be described later.

In the above described cylindrical substrate, when the relationship between gauge lengths L1 and L2 is adjusted within the range represented by Formula (1), it is possible to provide a cylindrical body for an implant having an excellent elasticity, flexibility and kink resistance (ability to be easily bent).

$$(L2-L1)/L1 \geq 0.1 \tag{1}$$

In (1), L1 represents a gauge length when the cylindrical substrate is compressed in the longitudinal direction thereof at a stress of 0.01 cN/dtex, wherein the gauge length is the distance between gauge lines drawn on the outer periphery of the cylindrical substrate, spaced apart by a distance 5 times the maximum value of the outer diameter of a woven fabric as measured without applying a stress to the cylindrical substrate; and L2 represents the gauge length when the cylindrical substrate is elongated in the longitudinal direction thereof at a stress of 0.01 cN/dtex.

When a cylindrical substrate is bent, a stress is applied to the inner peripheral side of the bent cylindrical substrate in the direction of compression and, at the same time, a stress is applied to the outer peripheral side thereof in the direction of elongation. In the above described cylindrical substrate, however, the outer periphery of the substrate can be sufficiently elongated with respect to the inner periphery thereof, due to adjusting the relationship between gauge lengths L1 and L2 within the above described range and, thus, the substrate has an excellent kink resistance.

Performing an elongation or compression operation at a stress of 0.01 cN/dtex generally corresponds to applying a stress equivalent to when a person elongates or compresses the cylindrical substrate in the longitudinal direction lightly by hand. This means, when the relationship between L1 and L2 is adjusted within the above described range, that the cylindrical substrate has a favorable maneuverability as well as an excellent elasticity and flexibility, even when a person performs a bending operation by hand.

The values of gauge lengths L1 and L2 of the cylindrical substrate can be measured in accordance with Measurement Example 6 to be described later. The value of (L2−L1)/L1 described above is preferably 0.15 or more, and more preferably 0.18 or more, since the elasticity and flexibility can be improved even more. Further, the value of (L2−L1)/L1 is preferably 1.0 or less.

The values of the outer diameter "a" upon compression and the outer diameter "b" upon elongation, of the cylindrical substrate, and the value of (a−b)/a, can be determined from the following a and b measured in accordance with Measurement Example 7 to be described later. "a" represents the outer diameter of the cylindrical substrate as measured when the cylindrical substrate is compressed in the longitudinal direction thereof at a stress of 0.01 cN/dtex; and "b" represents the outer diameter of the cylindrical substrate as measured when the cylindrical substrate is elongated in the longitudinal direction thereof at a stress of 0.01 cN/dtex. When the value of (a−b)/a is adjusted within the range represented in Formula (2), the difference in the inner diameter of the cylindrical substrate when the elongation and compression occur simultaneously, such as, for example, upon bending, is reduced, enabling to ensure a flow channel without variation. This prevents the occurrence of the turbulence of blood flow and the like, thereby inhibiting the thrombus formation.

$$0.03 \leq (a-b)/a < 0.2 \tag{2}$$

In Formula (2), "a" represents the outer diameter of the cylindrical substrate as measured when the cylindrical substrate is compressed in the longitudinal direction thereof at a stress of 0.01 cN/dtex; and "b" represents the outer diameter of the cylindrical substrate as measured when the cylindrical substrate is elongated in the longitudinal direction thereof at a stress of 0.01 cN/dtex.

The value of (a−b)/a is preferably 0.03 or more and less than 0.2, and more preferably 0.05 or more and less than 0.15, because the difference in the inner diameter of the cylindrical substrate when the elongation and compression occur simultaneously, such as, for example, upon bending, is reduced, enabling to ensure a flow channel without variation.

The surface roughness of the inner surface of the cylindrical substrate is defined as the difference between $D_s$ and $D_l$, when the distance between an arbitrary point on the outer surface of the cylindrical substrate and the intersection of a straight line extending from the arbitrary point on the outer surface toward the center of the cylindrical substrate with the inner surface, is defined as D; the shortest distance D in the cylindrical substrate is defined as $D_s$; and the longest distance D is defined as $D_l$. Further, the center of the cylindrical substrate refers to the point at which variation in the shortest distance from the center of the cylindrical substrate to the inner surface is minimized. The surface roughness of the inner surface of the cylindrical substrate is preferably 100 µm or less, more preferably 80 µm or less, and still more preferably 60 µm or less. The lower limit of the surface roughness of the inner surface is preferably 3 µm or more, from the viewpoint of facilitating endothelium formation when the cylindrical substrate is used as an artificial blood vessel. When the surface roughness of the inner surface of the cylindrical substrate is adjusted within the above described range, the turbulence of fluid does not occur, even if the cylindrical substrate has a small inner diameter. Particularly, even when using the cylindrical substrate as a narrow artificial blood vessel, there is an advantage that the turbulence of blood flow does not occur, and thrombi are less likely to be formed. The surface roughness of the inner surface of the cylindrical substrate can be measured in accordance with Measurement Example 8 to be described later.

The water permeability of the cylindrical substrate refers to the property in which, when a certain pressure is applied to the inner surface of the cylindrical substrate, water flows out through the outer surface. The value obtained by dividing the amount of water (mL) flowing out through the outer surface when a pressure of 16 kPa is applied to the inner surface, by the unit area (cm²) and the unit time (min.), is used as an index for evaluating the water permeability of the cylindrical substrate. The water permeability is measured in accordance with ISO 7198, by dividing the amount of water (mL) flowing out to the outer side of the cylindrical substrate when a pressure of 16 kPa is applied to the inner surface, by the unit area (cm²) and the unit time (min). When the water permeability of the cylindrical substrate is 5 mL/cm²/min. or more, the infiltration of cells and tissue is facilitated, after the degradation of the block copolymer; whereas when the water permeability is 500 mL/cm²/min. or less, the leakage of blood can be more easily prevented. Therefore, the water permeability under the conditions where a pressure of 16 kPa is applied to the inner surface is preferably 5 mL/cm²/min. to 500 mL/cm²/min., more preferably 50 mL/cm²/min. to 350 mL/cm²/min., and still more preferably 100 mL/cm²/min. to 250 mL/cm²/min.

Further, the cylindrical substrate preferably has a structure other than a bellows structure. When the cylindrical substrate has a structure other than a bellows structure, the inner surface of the cylindrical substrate has no surface roughness, and a turbulent flow does not occur even when a fluid flows through a narrow space. Particularly, when using the cylindrical substrate as a narrow artificial blood vessel, there is an advantage that the turbulence of blood flow does not occur, and thrombi are less likely to be formed. Specifically, the structure other than a bellows structure refers to a structure of a woven fabric formed by inserting a stem having a helical or annular corrugated groove(s) into a cylindrical article made of fibers, and has not been heat-set into a waveform or subjected to pleating.

The above described cylindrical substrate is a hollow substrate composed of any of the following materials, and examples of the material of the cylindrical substrate include synthetic polymers and natural polymers.

Examples of the synthetic polymer include polyethylene, polypropylene, polyvinyl chloride, polystyrene, polyvinyl acetate, polyvinylpyrrolidone, polyvinyl alcohol, polyurethane, PTFE, ePTFE, acrylic resins, polyamides, polyacetals, polycarbonates, polyesters and polysiloxanes; and mixtures and copolymers thereof. Examples of the natural polymer include polysaccharides, proteins and natural rubber, and examples of the proteins include gelatin and collagen.

The material of the cylindrical substrate as described above can be in any shape, and the shape of the material may be, for example, a film, a porous sheet, fibers or the like.

When the cylindrical substrate is composed of fibers, any of various types of organic fibers can be used. However, polyesters are preferred from the viewpoint of water absorbency and resistance to deterioration. Examples of the polyester include polyethylene terephthalate and polybutylene terephthalate. Further, a copolymerized polyester obtained by copolymerizing an aliphatic dicarboxylic acid, such as isophthalic acid, 5-sodium sulfoisophthalic acid or adipic acid, as an acid component, with polyethylene terephthalate or polybutylene terephthalate, may also be used.

The term "biodegradable polymer" as described above refers to a polymer having a property to be degraded in a living body. The term that can be used interchangeably with the "biodegradable" may be, for example, "bioabsorbable" or "biocompatible".

The above described block copolymer is characterized by being composed of a polyalkylene glycol block(s) and a polyhydroxyalkanoic acid block(s).

The polyalkylene glycol is a polymer in which one or more alkylene glycols are polymerized. Examples of the alkylene glycol include a polymer containing one or more of ethylene glycol, propylene glycol, oxyethylene glycol dimethyl ether, oxypropylene glycol monobutyl ether or oxypropylene glycol diacetate.

The polyhydroxyalkanoic acid is one in which one or more hydroxyalkanoic acids are polymerized. Examples of the hydroxyalkanoic acid include 2-hydroxypropionic acid (lactic acid), 2-hydroxybutanoic acid, 2-hydroxypentanoic acid, 2-hydroxyhexanoic acid, 3-hydroxybutanoic acid (3-hydroxybutyric acid), 3-hydroxypentanoic acid (3-hydroxyvaleric acid), 3-hydroxyhexanoic acid, 3-hydroxyheptanoic acid, 3-hydroxyoctanoic acid, 3-hydroxynonanoic acid, 3-hydroxydecanoic acid, 4-hydroxypentanoic acid, 4-hydroxyhexanoic acid, 4-hydroxyheptanoic acid, 4-hydroxyoctanoic acid, 5-hydroxyhexanoic acid, 5-hydroxyheptanoic acid, 6-hydroxyheptanoic acid, 6-hydroxyoctanoic acid, 8-hydroxynonanoic acid, 8-hydroxydecanoic acid, 9-hydroxydecanoic acid, 9-hydroxyundecanoic acid, 10-hydroxyundecanoic acid, 10-hydroxydodecanoic acid, 11-hydroxydodecanoic acid and 12-hydroxytridecanoic acid.

The ratio of the total mass of the alkylene glycol residue(s) with respect to the total mass of the block copolymer refers to the ratio of the total mass of the alkylene glycol residue(s) with respect to the mass of all the residues contained in the block copolymer, and is calculated from the numerical value obtained by $^1$H-NMR measurement, as described in Measurement Example 1 to be described later.

When the ratio of the total mass of the alkylene glycol residue(s) with respect to the total mass of the block copolymer is 5% or more, a suitable antithrombogenicity can be obtained; whereas when the ratio is 25% or less, a suitable swelling property can be obtained. Accordingly, to obtain both suitable antithrombogenicity and swelling property in a balanced manner, the ratio of the total mass of the alkylene glycol residue(s) with respect to the total mass of the block copolymer is preferably 5 to 25%, more preferably 8 to 22%, and still more preferably 10 to 20%.

The ratio of the total mass of the caprolactone residue(s) with respect to the total mass of the block copolymer refers to the ratio of the total mass of the caprolactone residue(s) with respect to the mass of all the residues contained in the block copolymer, and is calculated from the numerical value obtained by $^1$H-NMR measurement, as described in Measurement Example 1 to be described later. When the ratio of the total mass of the caprolactone residue(s) with respect to the total mass of the block copolymer is 15% or more, a suitable Young's modulus value can be obtained; whereas when the ratio is 80% or less, a suitable degradability can be obtained. Accordingly, to obtain both suitable degradability and Young's modulus in a balanced manner, the ratio of the total mass of the caprolactone residue(s) with respect to the total mass of the block copolymer is preferably 15 to 80%, more preferably 20 to 70%, and still more preferably 25 to 60%.

The ratio of the total mass of the glycolic acid residue(s) with respect to the total mass of the block copolymer refers to the ratio of the total mass of the glycolic acid residue(s) with respect to the mass of all the residues contained in the block copolymer, and is calculated from the numerical value obtained by $^1$H-NMR measurement, as described in Measurement Example 1 to be described later. The ratio of the total mass of the glycolic acid residue(s) with respect to the total mass of the block copolymer is preferably 10% or less, because a suitable Young's modulus value can be obtained, and the ratio is more preferably 7% or less, and still more preferably 5% or less.

The polyalkylene glycol block may be a single polyalkylene glycol molecule, or may be a plurality of polyalkylene glycol molecules connected via a linker(s). The polyalkylene glycol molecule(s) constituting the polyalkylene glycol block preferably have a weight average molecular weight of 7,000 to 170,000, more preferably 8,000 to 100,000, and still more preferably 10,000 to 50,000.

The Young's modulus of a film composed of the block copolymer can be evaluated in accordance with the method described in Measurement Example 2 to be described later. For the cylindrical body for an implant having been coated with the block copolymer to exhibit a favorable kink resistance, the film composed of the block copolymer preferably has a Young's modulus of 200 MPa or less, more preferably 100 MPa or less, and still more preferably 10 MPa or less.

The block copolymer needs to be formed into a film to coat the cylindrical substrate. Therefore, the block copolymer preferably has a weight average molecular weight of 10,000 or more. Although the upper limit is not particularly limited, the weight average molecular weight of the block copolymer is preferably 1,600,000 or less, more preferably 800,000 or less, and still more preferably 400,000 or less to improve formability. The weight average molecular weight can be determined by gel permeation chromatography (GPC), for example, by the method shown below.

The block copolymer is dissolved in chloroform, and passed through a 0.45 μm syringe filter (DISMIC-13HP; manufactured by ADVANTEC Co., Ltd.) to remove impurities and the like. Thereafter, the measurement is carried out by GPC, and the weight average molecular weight of the block copolymer is calculated.

Name of apparatus: Prominence (manufactured by Shimadzu Corporation)

Mobile phase: chloroform (for HPLC) (manufactured by Wako Pure Chemical Industries, Ltd.)

Flow velocity: 1 mL/min

Column: TSK gel GMHHR-M (diameter: 7.8 mm×length 300 mm; manufactured by Tosoh Corporation)

Detector: UV (254 nm), RI

Column, detector temperature: 35° C.

Reference material: polystyrene

The swelling property as described above refers to the property of a polymer to absorb water and swell, when dipped in water. The swelling ratio is used as an index to evaluate the swelling property.

The swelling ratio of a film composed of the block copolymer can be evaluated by the method described in Measurement Example 3 to be described later. When the swelling ratio of the film composed of the block copolymer is −10% or more, it is possible to prevent the peeling of the film from the cylindrical substrate, even if the film composed of the block copolymer has shrunk. When the swelling ratio is 20% or less, it is possible to prevent thrombus formation due to an excessive elongation of the cylindrical body for an implant, even if the film composed of the block copolymer has expanded. Accordingly, the swelling ratio of the film composed of the block copolymer is preferably −10% to 20%, more preferably −5% to 15%, and still more preferably 0% to 10%.

The polyhydroxyalkanoic acid block and the block copolymer can be synthesized, for example, by: a method in which a cyclic monomer is subjected to ring-opening polymerization in the presence of an initiator and a catalyst (ring-opening polymerization method); a method in which a molecule of the same or a different kind of block copolymer is bound to each of both ends of the block copolymer, one at a time, through their ends, in the presence of a catalyst or a condensing agent (multimerization method); and a method in which the ring-opening polymerization method and the multimerization method are combined.

Examples of the cyclic monomer include D,L-lactide, L-lactide, glycolide, D,L-lactide-co-glycolide, L-lactide-co-glycolide, ε-caprolactone, γ-butyrolactone, δ-valerolactone, ε-caprolactone-co-lactic acid and ε-caprolactone-co-glycolic acid-co-lactic acid.

Examples of the catalyst that can be used in the production by the ring-opening polymerization method include polymerization catalysts such as commonly used germanium-based catalysts, titanium-based catalysts, antimony-based catalysts and tin-based catalysts. Specific examples of such a polymerization catalyst include tin(II) octylate, trifluoride antimony, zinc powder, dibutyltin(IV) oxide and tin(II) oxalate. The method of adding the catalyst to a reaction system is not particularly limited. However, preferred is a method in which the catalyst is added during the charging of raw materials, in a state where the catalyst is dispersed in the raw materials, or alternatively, the catalyst is added at the time of starting decompression, in a dispersed state. The amount of the catalyst used is preferably 0.01 to 3% by weight, and more preferably 0.05 to 1.5% by weight, in terms of metal atoms, with respect to the total amount of the monomers to be used.

Examples of a metal catalyst that can be used in the production by the multimerization method include metals such as tin, titanium, lead, zinc, cobalt, iron, lithium and rare earth metals; and metal alkoxides, metal halogen compounds, organic carboxylates, carbonates, sulfates and oxides of these metals. However, a tin compound is preferred from the viewpoint of polymerization reactivity.

Examples of the tin compound that can be used include tin powder, tin(II) chloride, tin(IV) chloride, tin(II) bromide, tin(IV) bromide, ethoxytin(II), t-butoxytin(IV), isopropoxytin(IV), tin(II) acetate, tin(IV) acetate, tin(II) octylate, tin(II) laurate, tin(II) myristate, tin(II) palmitate, tin(II) stearate, tin(II) oleate, tin(II) linoleate, tin(II) acetylacetonate, tin(II) oxalate, tin(II) lactate, tin(II) tartrate, tin(II) pyrophosphate, tin(II) p-phenolsulfonate, tin(II) bis(methanesulfonate), tin (II) sulfate, tin(II) oxide, tin(IV) oxide, tin(II) sulfide, tin (IV) sulfide, dimethyltin(IV) oxide, methylphenyltin(IV) oxide, dibutyltin(IV) oxide, dioctyltin(IV) oxide, diphenyltin(IV) oxide, tributyltin oxide, triethyltin(IV) hydroxide, triphenyltin(IV) hydroxide, tributyltin hydride, monobutyltin(IV) oxide, tetramethyltin(IV), tetraethyltin(IV), tetrabutyltin(IV), dibutyldiphenyltin(IV), tetraphenyltin(IV), tributyltin(IV) acetate, triisobutyltin(IV) acetate, triphenyltin(IV) acetate, dibutyltin diacetate, dibutyltin dioctoate, dibutyltin(IV) dilaurate, dibutyltin(IV) maleate, dibutyltin bis(acetylacetonate), tributyltin(IV) chloride, dibutyltin dichloride, monobutyltin trichloride, dioctyltin dichloride, triphenyltin(IV) chloride, tributyltin sulfide, tributyltin sulfate, tin(II) methanesulfonate, tin(II) ethanesulfonate, tin(II) trifluoromethanesulfonate, ammonium hexachlorostannate (IV), dibutyltin sulfide, diphenyltin sulfide, triethyltin sulfate and tin(II) phthalocyanine.

Further, examples of a non-metal catalyst or the condensing agent that can be used in the production by the multimerization method include 4,4-dimethylaminopyridine, 4,4-dimethylaminopyridinium p-toluenesulfonate, 1-[3-(dimethylamino)propyl]-3-ethylcarbodiimide, 1-ethyl-3-(3-dimethylaminopropyl)carbodiimide hydrochloride, N,N'-dicyclohexylcarbodiimide, N,N'-diisopropylcarbodiimide, N,N'-carbonyldiimidazole, 1,1'-carbonyldi(1,2,4-triazole), 4-(4,6-dimethoxy-1,3,5-triazin-2-yl)-4-methylmorpholinium=chloride n-hydrate, (4,6-dimethoxy-1,3,5-triazin-2-yl)-(2-octoxy-2-oxoethyl)dimethylammonium trifluoromethanesulfonate, $^1$H-benzotriazol-1-yloxytris(dimethylamino)phosphonium hexafluorophosphate, $^1$H-benzotriazol-1-yloxytripyrrolidinophosphonium hexafluorophosphate, (7-azabenzotriazol-1-yloxy)tripyrrolidinophosphonium hexafluorophosphate, chlorotripyrrolidinophosphonium hexafluorophosphate, bromotris(dimethylamino)phosphonium hexafluorophosphate, 3-(diethoxyphosphoryloxy)-1,2,3-benzotriazin-4 (3H)-one, O-(benzotriazol-1-yl)-N,N,N',N'-tetramethyluronium hexafluorophosphate, O-(7-azabenzotriazol-1-yl)-N, N,N',N'-tetramethyluronium hexafluorophosphate, O—(N-succinimidyl)-N,N,N',N'-tetramethyluronium tetrafluoroborate, O—(N-succinimidyl)-N,N,N',N'-tetramethyluronium hexafluorophosphate, O-(3,4-dihydro-4-oxo-1,2,3-benzotriazine-3-yl)-N,N,N',N'-tetramethyluronium tetrafluoroborate, S-(1-oxide-2-pyridyl)-N,N,N',N'-tetramethyluronium tetrafluoroborate, O-[2-oxo-1(2H)-pyridyl]-N, N,N',N'-tetramethyluronium tetrafluoroborate, {{[(1-cyano-2-ethoxy-2-oxoethylidene)amino]oxy}-4-morpholinomethylene}dimethylammonium hexafluorophosphate, 2-chloro-1,3-dimethylimidazolinium hexafluorophosphate, 1-(chloro-1-pyrrolidinylmethylene) pyrrolidinium hexafluorophosphate, 2-fluoro-1,3-dimethylimidazolinium hexafluorophosphate, and fluoro-N,N,N',N'-tetramethylformamidinium hexafluorophosphate.

In performing the multimerization method, a linker molecule having two or more carboxyl groups, isocyanate groups, amino groups or hydroxyl groups may be used, at each end.

Examples of the linker molecule having two or more carboxyl groups include those having two or more carboxyl groups at their branching ends, among dicarboxylic acids, citric acid and multi-branched polymers; and acid halides, acid anhydrides and esters of the above described dicarboxylic acids, citric acid and multi-branched polymers. That is, the above described carboxylic acid groups may be converted to acid halide structures, ester structures or acid anhydride structures. Examples of the dicarboxylic acid include oxalic acid, malonic acid, succinic acid, glutaric acid, adipic acid, pimelic acid, suberic acid, azelaic acid, sebacic acid, malic acid, tartaric acid and dodecanedioic acid. Examples of the multi-branched polymer include hyper-branched polymers and dendrimers.

Examples of the linker molecule having two or more isocyanate groups include hexamethylene diisocyanate (HDI), 4,4'-diphenylmethane diisocyanate (MDI), 4,4'-dicyclohexylmethane diisocyanate, cyclohexyl diisocyanate (CHDI) and 2,4-toluene diisocyanate (TDI). Examples of the linker molecule having two or more amino groups include ethylenediamine, putrescine, cadaverine, hexamethylenediamine and phenylenediamine.

Examples of the linker molecule having two or more hydroxyl groups include ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol and oxoaliphatic diols.

When a linker molecule having a plurality of carboxyl, isocyanate, amino and hydroxyl groups within the same molecule is used as the above described linker molecule, a branched-chain copolymer can be synthesized in which the linker serves as a branching point. Examples of the linker molecule having a plurality of carboxyl, isocyanate, amino and hydroxyl groups within the same molecule include 2,2-bis(hydroxymethyl)propionic acid, malic acid and diamine diols.

By allowing a polyalkylene glycol (having hydroxyl groups at both ends) to react with any of the linker molecules to react in advance, or subjecting the hydroxyl groups to functional group conversion, it is possible to obtain a polyalkylene glycol having carboxyl groups, isocyanate groups or amino groups at both ends, or a polyalkylene glycol having carboxyl groups, isocyanate groups, or amino groups at one end, and these can be used as raw materials for producing the copolymer.

When the polymerization reaction is living, namely, when it is possible to initiate a polymerization reaction continuously from the ends of the polymer, the operation of adding monomers to the block copolymer solution after the completion of the polymerization reaction can be repeated, to perform the multimerization method.

The term "residue" is used to refer, in principle, to each of the repeating units of the chemical structures derived from the above described monomers, in the chemical structure of a block copolymer obtained by polymerizing two or more types of monomers including the monomers.

For example, when lactic acid ($CH_3CH(OH)COOH$) is polymerized with caprolactone (ε-caprolactone) represented by Chemical Formula (I), to form a block copolymer of lactic acid and caprolactone, a lactic acid residue has the structure represented by Chemical Formula (II), and a caprolactone residue has the structure represented by Chemical Formula (III).

As an exception, however, when a dimer of lactide or the like is used as a monomer, the "residue" refers to one of the two repeating structures derived from the dimer. For example, when dilactide ($_L$-(−)-lactide) represented by Chemical Formula (IV) is polymerized with caprolactone, the chemical structure of the resulting block copolymer includes a structure in which the structure represented by Chemical Formula (II) shown above is repeated twice, as a dilactide residue. In this example, one of the two repeating structures is taken as the lactic acid residue, and it is regarded that two lactic acid residues derived from dilactide are formed.

The properties of the block copolymer coated on the cylindrical substrate can be analyzed as follows. For example, the copolymer coated on the cylindrical substrate is dipped in a solvent such as chloroform, and the resulting extract is dried to obtain a solid. The resulting solid is subjected to measurements such as those described in Measurement Examples 1 to 3 to be described later.

The kink radius may be used, for example, as an index to evaluate the kink resistance. The "kink radius" as used herein refers, when a loop is formed with the cylindrical body for an implant and the diameter of the loop is gradually reduced, to the minimum loop radius of the loop at which buckling does not occur. The kink radius can be evaluated by the method described in Measurement Example 10 to be described later. Too large a kink radius may lead to an inability to conform to the movement of surrounding tissue after being implanted in a living body, or an inability to be implanted to a bent portion. The kink radius is preferably 15 mm or less, and more preferably 10 mm or less, because it facilitates the cylindrical body to conform to the movement of surrounding tissue after being implanted in a living body, and facilitates the implantation to a bent portion.

The coating thickness of the block copolymer refers to the thickness of the layer of the block copolymer in a cross section of the cylindrical body for an implant. The coating thickness of the block copolymer can be evaluated by the method described in Measurement Example 11 to be described later. When the coating thickness of the block copolymer is 1 μm or more, the pressure resistance can be improved; whereas when the coating thickness of the block copolymer is 500 μm or less, the block copolymer can be degraded in a suitable period of time. Accordingly, the coating thickness of the block copolymer is preferably 1 μm to 500 μm, more preferably 10 μm to 300 μm, and still more preferably 20 μm to 200 μm.

The cylindrical substrate preferably has an inner diameter of 1 to 10 mm, and more preferably 2 to 4 mm when the use as an artificial blood vessel or a stent graft is taken into consideration.

The artificial blood vessel is a medical device used to replace a diseased, living blood vessel, for example, one affected by arteriosclerosis, or form a by-pass or shunt. Examples of the material of the artificial blood vessel include fabrics, polytetrafluoroethylene, biomaterials and synthetic polymer materials. Among these, a fabric is preferred, because anticoagulant capacity can be easily imparted thereto.

The patency rate may be used, for example, as an index to evaluate an artificial blood vessel. It has been reported, in a human clinical setting, that the patency rate in using an artificial blood vessel as a substitute blood vessel, in a bypass surgery to obstruct arteriosclerosis in lower limbs, is 60%, whereas the patency rate in using an autologous vein is 80%. In cardiovascular implantation, such as a cardiac coronary artery bypass operation, an autologous vein, not an artificial blood vessel, is selected, taking into consideration the postoperative occlusion and stenosis. This means that the difference in the patency rate of about 20% in the cardiovascular implantation has a significant meaning in a clinical setting. However, the use of an autologous vein also entails a problem that it requires a removal surgery which imposes a heavy burden on patients, or that there are some patients whose quality of veins is too poor to be used to begin with. Therefore, an artificial blood vessel having a patency rate equal to or higher than that of an autologous vein, that is, an artificial blood vessel having a patency rate of 80% or more, has a great significance in a clinical setting.

The term "anticoagulant capacity" refers to the capacity to prevent the coagulation of blood and to inhibit thrombus formation. The anticoagulant capacity can be imparted, for example, by a method in which heparin or a heparin derivative is applied to the surface of the material.

The term "stent graft" refers to a medical device in which a stent and an artificial blood vessel (graft) are combined, and is used to treat aneurysm by being retained in a living blood vessel.

EXAMPLES

Our cylindrical members will now be described in specific detail, with reference to Reference Examples, Examples and Comparative Examples. However, this disclosure is in no way limited to the Examples.

Reference Example 1

A quantity of 50.0 g of L-lactide (PURASORB (registered trademark) L; manufactured by Purac Biomaterials), and 38.5 mL of F-caprolactone (manufactured by Wako Pure Chemical Industries, Ltd.), as monomers, were placed in a separable flask. Under an argon atmosphere, 0.29 g of tin(II)

octylate (manufactured by Wako Pure Chemical Industries, Ltd.), as a catalyst that had been dissolved in 14.5 mL of toluene (super dehydrated) (manufactured by Wako Pure Chemical Industries, Ltd.), and 90 µL of ion exchanged water as an initiator were added to the flask, and a promoter reaction was carried out at 90° C. for one hour. Thereafter, a copolymerization reaction was allowed to proceed at 150° C. for 6 hours to obtain a crude polyhydroxyalkanoic acid A.

The thus obtained crude polyhydroxyalkanoic acid A was dissolved in 100 mL of chloroform, and the resultant added dropwise to 1,400 mL of methanol in a stirred state, to obtain precipitates. The above described operation was repeated three times, and the resulting precipitates dried under reduced pressure at 70° C. to obtain a polyhydroxyalkanoic acid A.

A quantity of 14.2 g of the thus obtained polyhydroxyalkanoic acid A, 0.41 g of polyethylene glycol (weight average molecular weight: 10,000; manufactured by Sigma-Aldrich Inc.) having hydroxy groups at both ends, and 0.42 g of polyethylene glycol (weight average molecular weight: 10,200) having carboxyl groups at both ends were mixed. To the mixture, 0.56 g of 4,4-dimethylaminopyridinium p-toluenesulfonate (synthesized by the method described in Messmore, Benjamin W. et al., Journal of the American Chemical Society, 2004, 126, 14452), and 0.20 g of 4,4-dimethylaminopyridine (manufactured by Wako Pure Chemical Industries, Ltd.), as catalysts, were added. Under an argon atmosphere, the resulting mixture was dissolved in 28 mL of dichloromethane (dehydrated) (manufactured by Wako Pure Chemical Industries, Ltd.), and 2.06 g of dicyclohexylcarbodiimide (manufactured by Sigma-Aldrich Co.) as a condensing agent, that had been dissolved in 7 mL of dichloromethane added thereto, followed by condensation polymerization at room temperature for two days.

To the resulting reaction mixture, 60 mL of chloroform was added, and the resultant added dropwise to 1,000 mL of methanol in a stirred state to obtain precipitates. The resulting precipitates were dissolved in 100 mL of chloroform, and the resultant added dropwise to 1,000 mL of methanol in a stirred state to obtain precipitates. The above described operation was repeated twice to obtain a purified block copolymer of Reference Example 1, as precipitates.

Reference Example 2

A block copolymer of Reference Example 2 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 13.4 g, the added amount of the polyethylene glycol (weight average molecular weight: 10,000; manufactured by Sigma-Aldrich Inc.) having hydroxy groups at both ends was changed from 0.41 g to 0.82 g, and the added amount of the polyethylene glycol (weight average molecular weight: 10,200) having carboxyl groups at both ends changed from 0.42 g to 0.83 g.

Reference Example 3

A block copolymer of Reference Example 3 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 11.7 g, the added amount of the polyethylene glycol (weight average molecular weight: 10,000; manufactured by Sigma-Aldrich Inc.) having hydroxy groups at both ends was changed from 0.41 g to 1.63 g, and the added amount of the polyethylene glycol (weight average molecular weight: 10,200) having carboxyl groups at both ends changed from 0.42 g to 1.67 g.

Reference Example 4

A block copolymer of Reference Example 4 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 10.9 g, the added amount of the polyethylene glycol (weight average molecular weight: 10,000; manufactured by Sigma-Aldrich Inc.) having hydroxy groups at both ends was changed from 0.41 g to 2.04 g, and the added amount of the polyethylene glycol (weight average molecular weight: 10,200) having carboxyl groups at both ends changed from 0.42 g to 2.08 g.

Reference Example 5

A block copolymer of Reference Example 5 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 10.1 g, the added amount of the polyethylene glycol (weight average molecular weight: 10,000; manufactured by Sigma-Aldrich Inc.) having hydroxy groups at both ends was changed from 0.41 g to 2.45 g, and the added amount of the polyethylene glycol (weight average molecular weight: 10,200) having carboxyl groups at both ends changed from 0.42 g to 2.50 g.

Reference Example 6

A block copolymer of Reference Example 6 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 8.40 g, the added amount of the polyethylene glycol (weight average molecular weight: 10,000; manufactured by Sigma-Aldrich Inc.) having hydroxy groups at both ends was changed from 0.41 g to 3.27 g, and the added amount of the polyethylene glycol (weight average molecular weight: 10,200) having carboxyl groups at both ends changed from 0.42 g to 3.33 g.

Reference Example 7

A block copolymer of Reference Example 7 was obtained in the same manner as in Reference Example 1, except that, at the time of the addition of 0.20 g of 4,4-dimethylaminopyridine (manufactured by Wako Pure Chemical Industries, Ltd.), the added amount of the polyhydroxyalkanoic acid A was changed from 14.2 g to 6.75 g, the added amount of the polyethylene glycol (weight average molecular weight: 10,000; manufactured by Sigma-Aldrich Inc.) having hydroxy groups at both ends was changed from 0.41 g to 3.27 g, and the added amount of the polyethylene glycol (weight average molecular weight: 10,200) having carboxyl groups at both ends changed from 0.42 g to 3.33 g.

Reference Example 8

A quantity of 70.7 g of L-lactide (PURASORB (registered trademark) L; manufactured by Purac Biomaterials), and 19.0 g of glycolide (manufactured by Purac Biomaterials), as monomers, were placed in a separable flask. Under an argon atmosphere, 0.29 g of tin(II) octylate (manufactured by Wako Pure Chemical Industries, Ltd.), as a catalyst, which had been dissolved in 14.5 mL of toluene (super dehydrated) (manufactured by Wako Pure Chemical Industries, Ltd.), and 388 µL of ion exchanged water as an initiator were added to the flask, and a promoter reaction was carried out at 90° C. for one hour. Thereafter, a copolymerization reaction was allowed to proceed at 130° C. for 6 hours to obtain a crude polyhydroxyalkanoic acid 2.

The thus obtained crude polyhydroxyalkanoic acid 2 was dissolved in 100 mL of chloroform, and resultant was added dropwise to 1,400 mL of methanol in a stirred state to obtain precipitates. The above described operation was repeated three times, and the resulting precipitates dried under reduced pressure at 70° C. to obtain a polyhydroxyalkanoic acid 2.

A quantity of 9.81 g of the thus obtained polyhydroxyalkanoic acid 2, 5.22 g of the polyhydroxyalkanoic acid 1 obtained in Reference Example 1 were mixed. To the mixture, 0.56 g of 4,4-dimethylaminopyridinium p-toluenesulfonate (synthesized by the method described in Messmore, Benjamin W. et al., Journal of the American Chemical Society, 2004, 126, 14452), and 0.20 g of 4,4-dimethylaminopyridine (manufactured by Wako Pure Chemical Industries, Ltd.), as catalysts, were added. Under an argon atmosphere, the resulting mixture was dissolved in 28 mL of dichloromethane (dehydrated) (manufactured by Wako Pure Chemical Industries, Ltd.), and 2.06 g of dicyclohexylcarbodiimide (manufactured by Sigma-Aldrich Co.) as a condensing agent that had been dissolved in 7 mL of dichloromethane was added thereto, followed by condensation polymerization at room temperature for two days.

To the resulting reaction mixture, 60 mL of chloroform was added, and the resultant added dropwise to 1,000 mL of methanol in a stirred state to obtain precipitates. The resulting precipitates were dissolved in 100 mL of chloroform, and the resultant added dropwise to 1,000 mL of methanol in a stirred state to obtain precipitates. The above described operation was repeated twice to obtain a purified block copolymer of Reference Example 8, as precipitates.

Reference Example 9

A block copolymer of Reference Example 9 was obtained in the same manner as in Reference Example 8, except that, at the time of the addition of 0.56 g of 4,4-dimethylaminopyridinium p-toluenesulfonate (synthesized by the method described in Messmore, Benjamin W. et al., Journal of the American Chemical Society, 2004, 126, 14452), and 0.20 g of 4,4-dimethylaminopyridine (manufactured by Wako Pure Chemical Industries, Ltd.), the added amount of the polyhydroxyalkanoic acid 2 was changed from 9.81 g to 0.33 g, and the added amount of the polyhydroxyalkanoic acid 1 changed from 5.22 g to 14.7 g.

Since the added amount of the respective raw materials were changed, the molar ratios of the lactic acid residue, the glycolic acid residue, the caprolactone residue and the ethylene glycol residue in the block copolymers of the above described Reference Examples 1 to 9 were changed. Therefore, the molar ratio of each kind of residue was measured by hydrogen nuclear magnetic resonance ($^1$H-NMR), for each of the Reference Examples 1 to 9, and from the thus measured molar ratio, the ratio of the total mass of each of the lactic acid, caprolactone, glycolic acid and ethylene glycol residues, in each block copolymer, was calculated. The thus calculated values of Reference Examples 1 to 9 are shown in Table 1.

Measurement Example 1: Measurement of Mass Ratio of Each Residue by Hydrogen Nuclear Magnetic Resonance ($^1$H-NMR)

Each of the block copolymers of Reference Examples 1 to 9 was dissolved in deuterated chloroform, and the measurement carried out by $^1$H-NMR, using a JNM-EX270 (manufactured by JEOL Ltd.) at room temperature. Based on each peak in the resulting $^1$H-NMR spectra, the molar ratios of the lactic acid residue, the caprolactone residue and the ethylene glycol residue in each of the block copolymers of Reference Examples 1 to 9 were calculated. Specifically, in the lactic acid residue, the peak of the hydrogen atom (chemical shift value: about 5.2 ppm) of the methine group at the α-position is the characteristic peak, and thus the molar ratio of the residue was calculated based on the integral value of this peak with respect to the total signal. In the caprolactone residue, the peak of the hydrogen atoms (chemical shift value: about 2.3 ppm) of the methylene group at the α-position is the characteristic peak, and thus the molar ratio of the residue was calculated based on the integral value of this peak with respect to the total signal. In the glycolic acid residue, the peak of the hydrogen atoms (chemical shift value: about 4.8 ppm) of the methylene group at the α-position is the characteristic peak, and thus the molar ratio of the residue was calculated based on the integral value of this peak with respect to the total signal. In the ethylene glycol residue, the peak of four hydrogen atoms (chemical shift value: about 3.6 ppm) of the ethylene group is the characteristic peak, and thus the molar ratio of the residue was calculated based on the integral value of this peak with respect to the total signal.

From each of the molar ratios obtained as described above, the ratio of the total mass of each of the ethylene glycol, lactic acid, caprolactone and glycolic acid residues, in each of the block copolymers of Reference Examples 1 to 9, was calculated, in accordance with Formulae (3) to (7). The results are shown in Table 1.

$$W_{PEG}(\%) = (M_{EG} \times x_{EG})/Mx_{total} \times 100 \quad (3)$$

$$W_{PLA}(\%) = (M_{LA} \times x_{LA})/Mx_{total} \times 100 \quad (4)$$

$$W_{PCL}(\%) = (M_{CL} \times x_{CL})/Mx_{total} \times 100 \quad (5)$$

$$W_{PGA}(\%) = (M_{GA} \times x_{GA})/Mx_{total} \times 100 \quad (6)$$

$$Mx_{total} = M_{EG} \times x_{EG} + M_{LA} \times x_{LA} + M_{CL} \times x_{CL} + M_{GA} \times x_{GA} \quad (7)$$

$W_{PEG}$: ratio of total mass of ethylene glycol residue
$M_{EG}$: molecular weight of ethylene glycol residue
$x_{EG}$: molar ratio of ethylene glycol residue
$W_{PLA}$: ratio of total mass of lactic acid residue
$M_{LA}$: molecular weight of lactic acid residue
$x_{LA}$: molar ratio of lactic acid residue
$W_{PCL}$: ratio of total mass of caprolactone residue
$M_{CL}$: molecular weight of caprolactone residue
$x_{CL}$: molar ratio of caprolactone residue
$W_{PGA}$: ratio of total mass of glycolic acid residue
$M_{GA}$: molecular weight of glycolic acid residue
$x_{GA}$: molar ratio of glycolic acid residue A purified product of the block copolymer of each of Reference Examples 1 to 9 was dried under reduced pressure (100 Pa) at room temperature for 24 hours. Thereafter, each block copolymer was dissolved in chloroform to a concentration of 5% by weight, and the resulting solution transferred to a Petri dish made of Teflon, and dried under normal pressure at room temperature for 24 hours. The resultant was dried under reduced pressure (100 Pa) at room temperature for 24 hours to obtain a film composed of the block copolymer of each of Reference Examples 1 to 9.

Measurement Example 2: Tensile Test

To observe the properties of the film state, the Young's modulus of the resulting film composed of the block copolymer of each of Reference Examples 1 to 9 was measured. Specifically, the film composed of the block copolymer of each of Reference Examples 1 to 9 was cut in the form of a strip (50 mm×5 mm×0.1 mm), and set to a TENSILON universal tester RTM-100 (manufactured by Orientec Co., Ltd.) such that the distance between chucks in the length direction of the film was 10 mm. Subsequently, a tensile test was carried out under the following conditions A, in accordance with JIS K6251 (2010), and the slope of the stress/strain curve corresponding to the portion between two strain points of $\varepsilon 1=0.2\%$ and $\varepsilon 2=0.3\%$ was read, to determine the Young's modulus of (MPa) of the film composed of the block copolymer of each of Reference Examples 1 to 9. However, there are instances when the Young's modulus is calculated as the slope between two points or the slop determined by the least-squares method. The results are shown in Table 1.

Conditions A
  Name of apparatus: TENSILON Universal tensile tester RTM-100 (manufactured by Orientec Co., Ltd.)
  Initial length: 10 mm
  Tensile speed: 500 mm/min
  Load cell: 50 N
  Number of tests: 5 times Measurement Example 3: Measurement of Swelling Ratio To further observe the properties of the film state, the swelling ratio of the resulting film composed of the block copolymer of each of Reference Examples 1 to 9 is measured. Specifically, the film composed of the block copolymer of each of Reference Examples 1 to 9 was cut in the form of a strip (50 mm×5 mm×0.1 mm) in the same manner as in Measurement Example 2, placed in a plastic tube, and ion exchanged water (15 mL) added to thereto such that the entire film was immersed in the water. After shaking the plastic tube in an incubator controlled to 37° C. for 3 hours, the film was taken out of the tube, and the length of the long side of the film measured. From the thus measured long side length, the swelling ratio (%) of the film composed of the block copolymer of each of Reference Examples 1 to 9 was measured, using Formula (8). The results are shown in Table 1.

$$\text{Swelling ratio (\%)} = (Lw-Ld)/(Ld) \times 100 \quad (8)$$

Ld: long side length (cm) in a dry state (before being dipped in ion exchanged water)

Lw: long side length (cm) in a wet state (after being dipped in ion exchanged water)

TABLE 1

| | Measurement Example 1 | | | | | |
|---|---|---|---|---|---|---|
| | Ratio of total mass of ethylene glycol residue (wt %) | Ratio of total mass of lactic acid residue (wt %) | Ratio of total mass of caprolactone residue (wt %) | Ratio of total mass of glycolic acid residue (wt %) | Measurement Example 2 Young's modulus (MPa) | Measurement Example 3 Swelling ratio (%) |
| Reference Example 1 | 5 | 39 | 56 | 0 | 4.2 | 1.2 |
| Reference Example 2 | 11 | 52 | 37 | 0 | 5.1 | 9.0 |
| Reference Example 3 | 22 | 46 | 33 | 0 | 5.3 | 7.0 |
| Reference Example 4 | 25 | 30 | 45 | 0 | 6.9 | 14.7 |
| Reference Example 5 | 28 | 42 | 30 | 0 | 9.8 | 24.0 |
| Reference Example 6 | 38 | 25 | 37 | 0 | 24.4 | 35.2 |
| Reference Example 7 | 49 | 20 | 31 | 0 | 33.6 | 58.0 |
| Reference Example 8 | 0 | 61 | 27 | 12 | 211.4 | Not measured |
| Reference Example 9 | 0 | 39 | 61 | 1 | 2.7 | −2.0 |
| Reference Example 14 | 11 | 24 | 65 | 0 | 6.5 | 5.5 |
| Reference Example 15 | 32 | 19 | 49 | 0 | 15.3 | 26.7 |

Reference Example 10: Preparation of Cylindrical Substrate A

The following warps (warp A and warp B) and wefts (weft C and weft D) were used in the weaving process.
  Warp A (sea-island composite fibers): polyethylene terephthalate fibers, 66 dtex, 9 filaments (after sea removal treatment: 52.8 dtex, 630 filaments)
  Warp B (soluble yarns): polyester fibers made of a polyester copolymerized with 5-sodium sulfoisophthalic acid, and easily soluble in alkali, 84 dtex, 24 filaments
  Weft C (inner layer) (sea-island composite fibers): polyethylene terephthalate fibers, 66 dtex, 9 filaments (after sea removal treatment: 52.8 dtex, 630 filaments)
  Weft D (outer layer): polyethylene terephthalate fibers, 56 dtex, 18 filaments The tension of the warp B was set to 0.9 cN/dtex, and the tension of the warp A was set to 0.1 cN/dtex, during weaving, and a cylindrical woven fabric having an inner diameter of 3.3 mm was woven such that the weaving density after post processing of the warp A would be 201 pieces/inch (2.54 cm), that of the weft C would be 121 pieces/inch (2.54 cm), and that of the weft D would be 121 pieces/inch (2.54 cm). The warp A and the warp B were arranged at such a ratio that one piece of the warp B was arranged with respect to 3 pieces of the warp A. Further, the warp B was arranged between the weft C located at the inner layer and the weft D located at the outer layer.

Subsequently, the post processing was carried out by the following steps to obtain a cylindrical substrate A.
(a) Washing with Hot Water The treatment was carried out under the conditions of a temperature of 98° C. and for a period of 20 minutes.
(b) Pre-Heat Setting A round-bar having an outer diameter of 2.8 mm was inserted into the cylindrical woven fabric, both ends were fixed with wires, and a heat treatment was carried out. The treatment was carried out under the conditions of a temperature of 180° C. and a period of 5 minutes. The material of the round-bar was SUS.
(c) Sea Removal Treatment The sea removal treatment of the warp A and the weft C, as well as the dissolution and removal of the warp B were carried out.
(c-1) Acid Treatment Maleic acid was used as the acid. The treatment was carried out under the conditions of an acid concentration of 0.2% by mass, a temperature of 130° C., and a period of 30 minutes
(c-2) Alkali Treatment Sodium hydroxide was used as the alkali. The treatment was carried out under the conditions of an alkali concentration of 1% by mass, a temperature of 80° C., and a period of 90 minutes.
(d) Heat Setting (First Time)

The round-bar having an outer diameter of 3.3 mm was inserted into the cylindrical woven fabric, both ends were fixed with wires or the like in a state where the cylindrical woven fabric was maximumly compressed, with care not to cause wrinkles in the warp direction, and a heat treatment was carried out. The treatment was carried out under the conditions of a temperature of 180° C. and a period of 5 minutes. The material of the round-bar was SUS.
(e) Heat Setting (Second Time)

The round-bar having an outer diameter of 3.3 mm was inserted into the cylindrical woven fabric, both ends were fixed with wires or the like in a state where the cylindrical woven fabric was elongated 30% in the warp direction, and a heat treatment was carried out. The treatment was carried out under the conditions of a temperature of 170° C. and a period of 5 minutes. The material of the round-bar was SUS.

Reference Example 11: Preparation of Cylindrical Substrate B

A cylindrical substrate was prepared in the same manner as in Reference Example 10, except that the round-bar to be used in the heat setting (first time) and the heat setting (second time) was changed from the round-bar having an outer diameter of 3.3 mm to one having an outer diameter of 3.0 mm, and further, that both ends were fixed with wires without elongating the cylindrical woven fabric in the warp direction, instead of being fixed in a state elongated 30% in the warp direction, in the heat setting (second time), to obtain a cylindrical substrate B.

Reference Example 12: Preparation of Cylindrical Substrate C

As polyester fibers constituting the outer layer of the cylindrical substrate, monofilaments having a single fiber fineness of 180 dtex (diameter: 0.13 mm), and multifilaments having a single fiber fineness of 2.33 dtex and a total fineness of 56 dtex, were prepared. At the time of weaving, the multifilaments were used as the warp, and the monofilaments were used as the weft. Further, as polyester fibers constituting the inner layer of the cylindrical substrate, multifilaments A' were used. The multifilaments A' are sea-island fibers (in which the sea/island ratio (mass ratio) is 20/80, and the number of island components is 70) that include a sea-component polymer composed of polyethylene terephthalate copolymerized with 5-sodium sulfoisophthalic acid, and an island component polymer composed of polyethylene terephthalate, and which have a single fiber fineness of 7.3 dtex and a total fineness of 66 dtex. The above described multifilaments A' will be converted into multifilaments A by being subjected to an extra-fine treatment. These filaments were used as the warp and the weft at the time of weaving.

Using the above described fibers, a multi-layered cylindrical woven fabric having an inner diameter of 3.3 mm was woven on a shuttle loom, and scouring carried out at 98° C. Subsequently, the woven fabric was treated with a 4% by mass aqueous solution of sodium hydroxide at 98° C. for 20 minutes, to completely dissolve and remove the sea component in the above described sea-island composite fibers so that the multifilaments A' were converted into extra-fine multifilaments having a single fiber fineness of 0.08 dtex (single fiber diameter of 2.9 m) and a total fineness of 53 dtex. Thereafter, the resulting cylindrical woven fabric was dried at a dry heat of 120° C., and heat-set in the form of a cylinder at 170° C. with a rod-like fixture being inserted thereinto, to obtain a cylindrical substrate C having a weft density of the outer layer of 21 pieces/2.54 cm, and a weft density of the inner layer of 336 pieces/2.54 cm.

Reference Example 13: Preparation of Cylindrical Substrate D

As polyester fibers constituting the outer layer of the cylindrical substrate, monofilaments having a single fiber fineness of 108 dtex (diameter: 0.11 mm), and multifilaments having a single fiber fineness of 2.33 dtex and a total fineness of 56 dtex, were prepared. At the time of weaving, the multifilaments were used as the warp, and the monofilaments were used as the weft. Further, as polyester fibers constituting the inner layer of the cylindrical substrate, multifilaments having a single fiber fineness of 0.23 dtex (single fiber diameter: 4.7 μm) and a total fineness of 33 dtex were prepared. These filaments were used as the warp and the weft at the time of weaving.

Using the above described fibers, a multi-layered cylindrical woven fabric having an inner diameter of 3.3 mm was woven on a shuttle loom, and scouring was carried out at 98° C. Thereafter, the resulting cylindrical woven fabric was dried at a dry heat of 120° C., and heat-set in the form of a cylinder at 170° C. with a rod-like fixture being inserted thereinto, to obtain a cylindrical substrate D having a weft density of the outer layer of 76 pieces/2.54 cm, and a weft density of the inner layer of 230 pieces/2.54 cm.

The tests of the following Measurement Examples 4 to 9 were carried out for each of the above described cylindrical substrates A to D, to measure: the elongation rate (%) under a load of 20 N; the inner diameter (mm); the outer diameter (mm); the gauge length L1 (mm) upon compression; the gauge length L2 (mm) upon elongation; the value of (L2−L1)/L1, the outer diameter "a" upon compression; the outer diameter "b" upon elongation; the value of (a−b)/a; the surface roughness of the inner surface (m); and the water permeability (mL/cm$^2$/min.) under a pressure of 16 kPa; of each of the cylindrical substrate A to D. The thus measured values are shown in Tables 2 and 3. The ratio of the mass of the block copolymer coated on each of the cylindrical substrates A to D, with respect to the mass of each of the cylindrical substrates A to D, is less than 1%.

The ratio of the mass of the block copolymer included in the coated cylindrical body with respect to the mass of the cylindrical substrate can be measured by the following method.

Pieces of the coated cylindrical body each having a length of 0.5 cm in the longitudinal direction are cut out, from arbitrarily selected three locations of the coated cylindrical body, and the thus cut out pieces of the coated cylindrical body are dissolved in an organic solvent. The resulting solution is subjected to a $^1$H-NMR measurement at room temperature, using a JNM-EX270 (manufactured by JEOL Ltd.). Based on each peak in the resulting $^1$H-NMR spectra, the ratio of the mass of the block copolymer with respect to the mass of the cylindrical substrate is calculated. Specifically, in an ethylene terephthalate residue, the peak of the hydrogen atoms of the benzene ring (chemical shift value: about 8.2 ppm) is the characteristic peak, and thus the molar ratio of the residue is calculated based on the integral value of this peak with respect to the total signal. In the lactic acid residue, the peak of the hydrogen atom (chemical shift value: about 5.2 ppm) of the methine group at the α-position is the characteristic peak, and thus the molar ratio of the residue is calculated based on the integral value of this peak with respect to the total signal. In the caprolactone residue, the peak of the hydrogen atoms (chemical shift value: about 2.3 ppm) of the methylene group at the α-position is the characteristic peak, and thus the molar ratio of the residue is calculated based on the integral value of this peak with respect to the total signal. In the glycolic acid residue, the peak of the hydrogen atoms (chemical shift value: about 4.8 ppm) of the methylene group at the α-position is the characteristic peak, and thus the molar ratio of the residue is calculated based on the integral value of this peak with respect to the total signal. In the ethylene glycol residue, the peak of four hydrogen atoms (chemical shift value: about 3.6 ppm) of the ethylene group is the characteristic peak, and thus the molar ratio of the residue is calculated based on the integral value of this peak with respect to the total signal.

From the molar ratios obtained as described above, the mass ratio of the block copolymer coated on each of the cylindrical substrates A to D, with respect to the weight of each of the cylindrical substrates A to D, was calculated, in accordance with Formulae (7) and (9).

$$W_{cop}(\%) = Mx_{total}/(M_{ET} \times x_{ET}) \times 100 \quad (9)$$

$$Mx_{total} = M_{EG} \times x_{EG} + M_{LA} \times x_{LA} + M_{CL} \times x_{CL} + M_{GA} \times x_{GA} \quad (7)$$

$W_{cop}$: mass ratio of block copolymer coated on cylindrical substrate with respect to mass of cylindrical substrate
$M_{ET}$: molecular weight of ethylene terephthalate residue
$x_{ET}$: molar ratio of ethylene terephthalate residue The organic solvent to be used is not particularly limited, and any organic solvent capable of dissolving both the cylindrical substrate and the block copolymer can be used. However, 1,1,1,3,3,3-hexafluoroisopropanol-D2 is preferably used.

Measurement Example 4: Elongation Rate Under Load of 20N

Each of the cylindrical substrates A to D was cut into a length of 150 mm in the longitudinal direction, and set to a dual-column desk top tester, INSTRON 5965 (manufactured by Instron Japan Co., Ltd.) such that the distance between chucks in the longitudinal direction was 100 mm. Then, a tensile test was carried out under the following conditions B, in accordance with ISO 7198 (2016). Thereafter, the elongation rate (%) under a load of 20 N of each of the cylindrical substrates A to D was determined, in accordance with Formula (10).

Conditions B
Name of apparatus: a dual-column desktop tester, INSTRON 5965 (manufactured by Instron Japan Co., Ltd.)
Initial length: 100 mm
Tensile speed: 50 mm/min
Load cell: 1 kN
Number of tests: 5 times Elongation rate (%)=length (mm) of cylindrical substrate under a load of 20N/initial length (mm)× 100 (10)

Measurement Example 5: Measurement of Inner Diameter and Outer Diameter of Cylindrical Substrates A to D The inner diameter of each of the cylindrical substrates A to D was measured in accordance with the guidance of ISO 7198. Specifically, a cone having a degree of taper of 1/10 or less was erected vertically, and a sample of each cylindrical substrate was dropped gently and vertically on top of the cone such that the cross section in the radial direction of the sample fell upon the cone. Thereafter, the diameter of the cone at the position corresponding to the lower end of the sample staying on the cone was measured. Each cylindrical substrate was cut at five locations at intervals of 50 mm in the longitudinal direction, to carry out the measurement, and the mean value of the measured results was taken as the inner diameter (mm) of each of the cylindrical substrates A to D. Further, the outer diameter of each of the cylindrical substrates A to D was measured at five locations at intervals of 50 mm in the longitudinal direction without applying a stress to the cylindrical substrate, using a pair of vernier calipers, and the mean value of the measured results was taken as the outer diameter (mm) of each of the cylindrical substrates A to D. The results are shown in Table 2.

Figure 1:
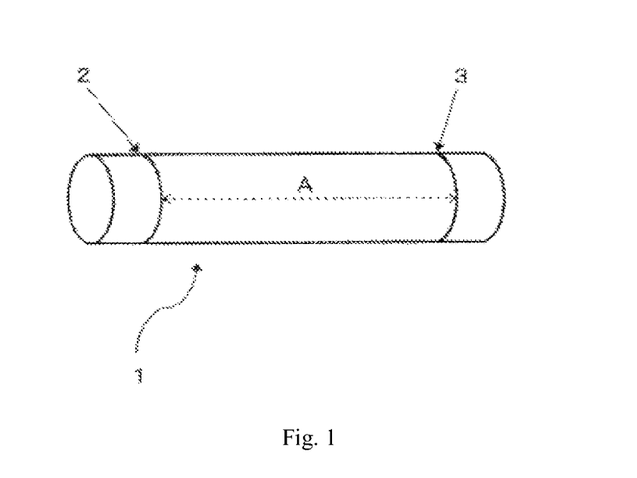
FIG. 1 is an explanatory diagram for drawing gauge lines on a cylindrical substrate.

Measurement Example 6: Measurement of Gauge Length L1 Upon Compression and Gauge Length L2 Upon Elongation, of Cylindrical Substrate Based on the outer diameter (mm) of each of the cylindrical substrates A to D, which was obtained in Measurement Example 5 without applying a stress to the cylindrical substrate, the gauge length (mm) upon compression was measured. FIG. 1 is an explanatory diagram for drawing gauge lines on the cylindrical substrate. As shown in FIG. 1, a first gauge line 2 was drawn on the outer periphery of the cylindrical substrate, at a position 5 mm from one end of the substrate. Further, a second gauge line 3 was drawn on the outer periphery of the cylindrical substrate, at a position spaced apart from the first gauge line by distance A, which is 5 times the maximum value of the outer diameter of the cylindrical substrate. The cylindrical substrate is cut in the radial direction at a position 5 mm from the second gauge line.

Figure 2:
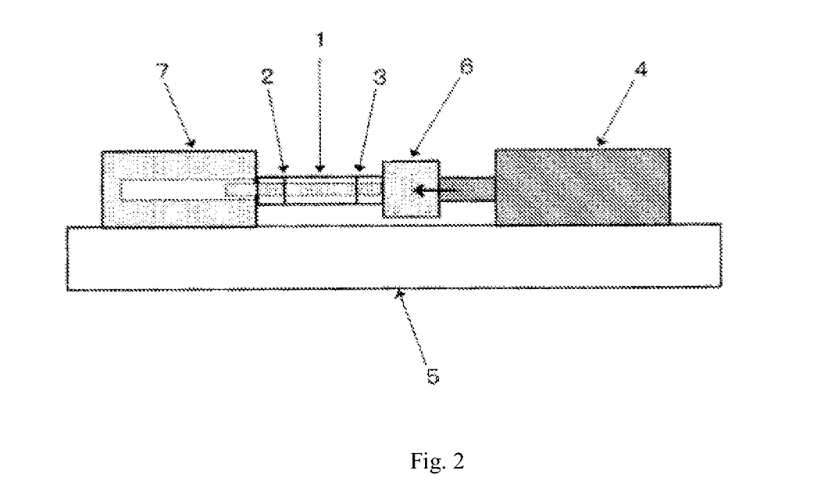
FIG. 2 is a schematic diagram of an apparatus for measuring the gauge length upon compression of the cylindrical substrate.

FIG. 2 is a schematic diagram of the apparatus for measuring the gauge length (mm) upon compression of each of the cylindrical substrates A to D. In this apparatus, as shown in FIG. 2, a HANDY DIGITAL FORCE GAUGE HF-1 (rated capacity: 10 N) manufactured by Japan Instrumentation System Co., Ltd., as a load measuring device (force gauge) 4, is disposed on a frame 5; a chuck fixture 6 for compression including a core rod portion is attached to the load measuring device 4; and a receiving fixture 7 for compression provided with a hole into which the core rod portion can be inserted, is attached to the frame 5. Each of the cylindrical substrates A to D was set on the above described apparatus such that the core rod portion of the chuck fixture 6 for compression was inserted therethrough, and the gauge length L1 (gauge length upon compression) when compressed in the longitudinal direction at a stress of 0.01 cN/dtex was measured, using a pair of vernier calipers.

Figure 3:
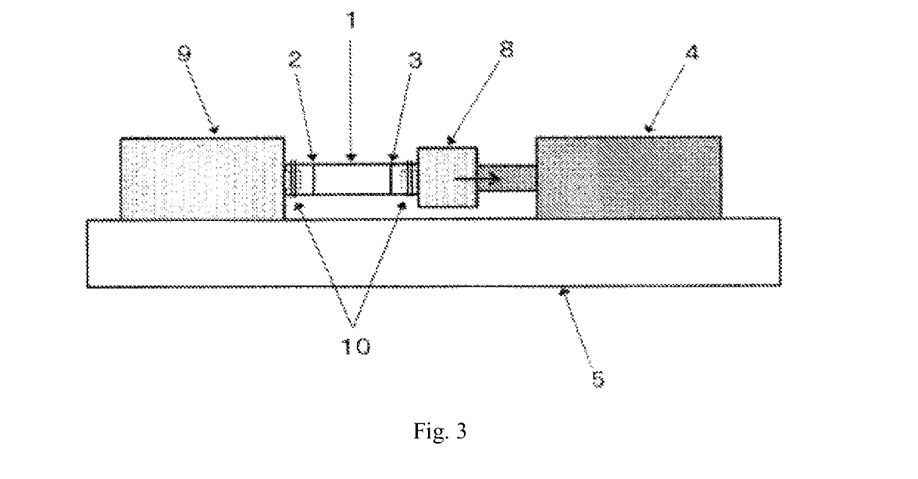
FIG. 3 is a schematic diagram of an apparatus for measuring the gauge length upon elongation of the cylindrical substrate.

The core rod portion of the chuck fixture 6 for compression, which is to be inserted into a cylindrical substrate 1, has an inner diameter that is 0.1 mm (±0.03 mm) smaller than the inner diameter of the cylindrical substrate 1, and the hole of the receiving fixture 7 for compression has the same diameter as the inner diameter of the cylindrical substrate. The "same diameter" as used herein does not necessarily have to be strictly the same diameter, and a diameter with a difference within the range of about ±0.03 mm is included in the definition of the same diameter. FIG. 3 is a schematic diagram of the apparatus for measuring the gauge length upon elongation of the cylindrical substrate. In this apparatus, as shown in FIG. 3, a HANDY DIGITAL FORCE GAUGE HF-1 (rated capacity: 10 N) manufactured by Japan Instrumentation System Co., Ltd., as the load measuring device (force gauge) 4, is disposed on the frame 5; a chuck fixture 8 for elongation is attached to the load measuring device 4, and a receiving fixture 9 for elongation is attached to the frame 5. The portions of the cylindrical substrate 1 on the outer sides of the gauge lines are fixed with strings 10, and the gauge length L2 (gauge length upon elongation) when the cylindrical substrate was elongated in the longitudinal direction at a stress of 0.01 cN/dtex was measured, using a pair of vernier calipers. The results are shown in Table 3.

Measurement Example 7: Measurement of Outer Diameter a Upon Compression, Outer Diameter b Upon Elongation and Value of (a−b)/a The core rod portion of the chuck fixture 6 was inserted through each of the cylindrical substrates A to D for compression shown in FIG. 2, to be set to the apparatus shown in FIG. 2. Then the outer diameter of each of the cylindrical substrates A to D was measured at five locations at intervals of 50 mm in the longitudinal direction in a state where the cylindrical substrate was compressed at a stress of 0.01 cN/dtex in the longitudinal direction, using a pair of vernier calipers. The mean value of the measured results was taken as the "outer diameter a upon compression" of each of the cylindrical substrates A to D. Further, each of the cylindrical substrates A to D was inserted over the core rod portion of the chuck fixture 6 for compression shown in FIG. 2, to be set to the apparatus shown in FIG. 2. Then the outer diameter of each of the cylindrical substrates A to D was measured at five locations at intervals of 50 mm in the longitudinal direction, in a state where the cylindrical substrate was elongated at a stress of 0.01 cN/dtex in the longitudinal direction, using a pair of vernier calipers. The mean value of the measured results was taken as the "outer diameter b upon elongation" of each of the cylindrical substrates A to D.

From the outer diameter a upon compression of each of the cylindrical substrates A to D and the outer diameter b upon elongation of each of the cylindrical substrates A to D, obtained as described above, the value of (a−b)/a was determined for each cylindrical substrate. The results are shown in Table 3.

Figure 4:
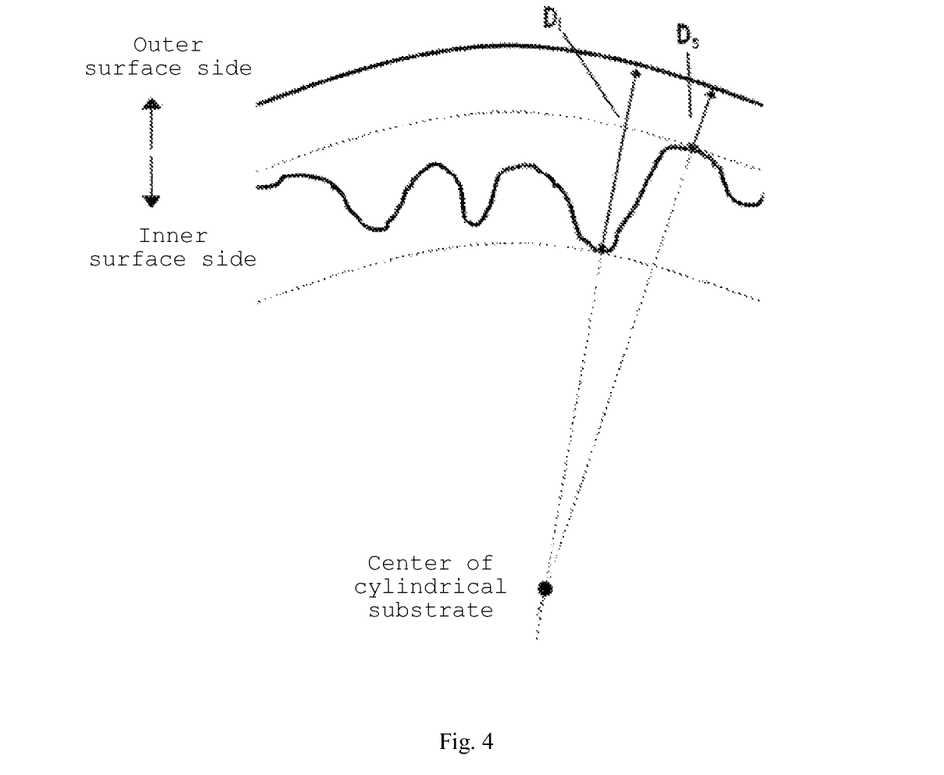
FIG. 4 is an explanatory diagram for measuring the surface roughness of the inner surface of the cylindrical substrate.

Measurement Example 8: Surface Roughness of Inner Surface of Cylindrical Substrate A cross section in the longitudinal direction of each of the cylindrical substrates A to D was enlarged 150-fold by an electron microscope, to capture an image. In the resulting image, $D_s$ and $D_l$ of the inner surface of each of the cylindrical substrates A to D were measured, and the surface roughness of the inner surface was determined from the difference between $D_s$ and $D_l$. FIG. 4 shows examples of $D_s$ and $D_l$. The measurement was carried out five times, in different visual fields, and the mean value of the measured values was used for the evaluation. The thus obtained mean value was defined as the "surface roughness of the inner surface of the cylindrical substrate". The results are shown in Table 3.

Measurement Example 9: Water Permeability

Joints (manufactured by Isys) were attached on both ends of each of the cylindrical substrates A to D, and silicone tubes were connected thereto. While allowing water to flow from one of the silicone tubes such that a pressure of 16 kPa was applied to the inner surface of the cylindrical substrate, the other silicone tube was clamped with forceps to prevent water from flowing out of the silicone tube. Water was allowed to flow in this state for one minute, and the amount of water (mL) flown out through the outer surface of each of the cylindrical substrates A to D was measured. The thus measured value was divided by the area (cm$^2$) of the outer surface of each of the cylindrical substrates A to D, and by the period of time during which water had been allowed to flow (min.), and the water permeability (mL/cm$^2$/min.) under a pressure of 16 kPa of each of the cylindrical substrates A to D was determined from the resulting value. The results are shown in Table 3.

TABLE 2

|  | Measurement Example 4 Elongation rate under a load of 20 N (%) | Measurement Example 5 Inner diameter (mm) | Measurement Example 5 Outer diameter (mm) | Measurement Example 6 Gauge length (mm) | Measurement Example 6 Gauge length upon compression L1 (mm) | Measurement Example 6 Gauge length upon elongation L2 (mm) | (L2−L1)/L1 |
|---|---|---|---|---|---|---|---|
| Cylindrical substrate A | 15 | 3.29 | 4.04 | 20.1 | 17.2 | 21.8 | 0.27 |
| Cylindrical substrate B | 45 | 3.04 | 3.75 | 18.8 | 16.5 | 20.5 | 0.24 |

TABLE 2-continued

| | Measurement Example 4 Elongation rate under a load of 20 N (%) | Measurement Example 5 | | Measurement Example 6 | | |
|---|---|---|---|---|---|---|
| | | Inner diameter (mm) | Outer diameter (mm) | Gauge length (mm) | Gauge length upon compression L1 (mm) | Gauge length upon elongation L2 (mm) | (L2-L1)/L1 |
| Cylindrical substrate C | 2 | 3.32 | 4.22 | 20.5 | 20.4 | 20.7 | 0.01 |
| Cylindrical substrate D | 2 | 3.30 | 4.23 | 20.2 | 20.2 | 20.3 | 0.00 |

TABLE 3

| | Measurement Example 7 | | | Measurement Example 8 | Measurement Example 9 |
|---|---|---|---|---|---|
| | Outer diameter a upon compression (mm) | Outer diameter b upon elongation (mm) | (a - b)/a | Surface roughness of inner surface (µm) | Water permeability under a pressure of 16 kPa (mL/cm²/min) |
| Cylindrical substrate A | 4.25 | 3.97 | 0.07 | 58 | 194 |
| Cylindrical substrate B | 3.96 | 3.69 | 0.07 | 61 | 188 |
| Cylindrical substrate C | 4.22 | 4.21 | 0.00 | 271 | 67 |
| Cylindrical substrate D | 4.24 | 4.24 | 0.00 | 220 | 68 |

Example 1

The block copolymer of Reference Example 1 was dissolved in chloroform to prepare a solution having a concentration of 2000 by weight. The resulting solution was coated on the cylindrical substrate A composed of the polyethylene terephthalate fibers to form a coating layer to obtain a coated cylindrical body of Example 1.

Example 2

A coated cylindrical body was prepared in the same manner as in Example 1, except that the block copolymer of Reference Example 2 was used instead of the block copolymer of Reference Example 1. Specifically, the block copolymer of Reference Example 2 was dissolved in chloroform to prepare a solution having a concentration of 200% by weight. The resulting solution was coated on the cylindrical substrate A composed of the polyethylene terephthalate fibers to form a coating layer to obtain a coated cylindrical body of Example 2.

Example 3

A coated cylindrical body was prepared in the same manner as in Example 1, except that the block copolymer of Reference Example 3 was used instead of the block copolymer of Reference Example 1. Specifically, the block copolymer of Reference Example 3 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Example 3.

Example 4

A coated cylindrical body was prepared in the same manner as in Example 1, except that the block copolymer of Reference Example 4 was used instead of the block copolymer of Reference Example 1. The measurement was carried out. Specifically, the block copolymer of Reference Example 4 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Example 4.

Example 5

A coated cylindrical body was prepared in the same manner as in Example 2, except that the cylindrical substrate B composed of the polyethylene terephthalate fibers was used instead of the cylindrical substrate A composed of the polyethylene terephthalate fibers. Specifically, the block copolymer of Reference Example 2 was dissolved in chloroform to prepare a solution having a concentration of 20% by weight. The resulting solution was coated on the cylindrical substrate B described above to form a coating layer to obtain a coated cylindrical body of Example 5.

Comparative Example 1

A coated cylindrical body was prepared in the same manner as in Example 1, except that the block copolymer of Reference Example 5 was used instead of the block copolymer of Reference Example 1. Specifically, the block copolymer of Reference Example 5 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 1.

Comparative Example 2

A coated cylindrical body was prepared in the same manner as in Example 1, except that the block copolymer of Reference Example 6 was used instead of the block copolymer of Reference Example 1. Specifically, the block copolymer of Reference Example 6 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 2.

Comparative Example 3

A coated cylindrical body was prepared in the same manner as in Example 1, except that the block copolymer of Reference Example 7 was used instead of the block copolymer of Reference Example 1. Specifically, the block copolymer of Reference Example 7 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 3.

Comparative Example 4

A coated cylindrical body was prepared in the same manner as in Example 1, except that the block copolymer of Reference Example 8 was used instead of the block copolymer of Reference Example 1. Specifically, the block copolymer of Reference Example 8 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 4.

Comparative Example 5

A coated cylindrical body was prepared in the same manner as in Example 1, except that the block copolymer of Reference Example 9 was used instead of the block copolymer of Reference Example 1. Specifically, the block copolymer of Reference Example 9 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 5.

Comparative Example 6

A coated cylindrical body was prepared in the same manner as in Example 1, except that the cylindrical substrate B was used instead of the cylindrical substrate A, and further that the block copolymer of Reference Example 5 was used instead of the block copolymer of Reference Example 1. Specifically, the block copolymer of Reference Example 5 was dissolved in chloroform to prepare a solution having a concentration of 20% by weight. The resulting solution was coated on the cylindrical substrate B composed of the polyethylene terephthalate fibers to form a coating layer to obtain a coated cylindrical body of Comparative Example 6.

Comparative Example 7

A coated cylindrical body was prepared in the same manner as in Example 2, except that the cylindrical substrate C was used instead of the cylindrical substrate A. Specifically, the block copolymer of Reference Example 2 was dissolved in chloroform to prepare a solution having a concentration of 20% by weight. The resulting solution was coated on the cylindrical substrate C composed of the polyethylene terephthalate fibers to form a coating layer to obtain a coated cylindrical body of Comparative Example 7.

Comparative Example 8

A coated cylindrical body was prepared in the same manner as in Example 1, except that the cylindrical substrate C was used instead of the cylindrical substrate A, and further that the block copolymer of Reference Example 5 was used instead of the block copolymer of Reference Example 1. Specifically, the block copolymer of Reference Example 5 was dissolved in chloroform to prepare a solution having a concentration of 20% by weight. The resulting solution was coated on the cylindrical substrate C composed of the polyethylene terephthalate fibers to form a coating layer to obtain a coated cylindrical body of Comparative Example 8.

Comparative Example 9

A coated cylindrical body was prepared in the same manner as in Example 2, except that the cylindrical substrate D was used instead of the cylindrical substrate A. Specifically, the block copolymer of Reference Example 2 was dissolved in chloroform to prepare a solution having a concentration of 20% by weight. The resulting solution was coated on the cylindrical substrate D composed of the polyethylene terephthalate fibers to form a coating layer to obtain a coated cylindrical body of Comparative Example 9.

Reference Example 14

A quantity of 25.0 g of L-lactide (PURASORB (registered trademark) L; manufactured by Purac Biomaterials), and 57.8 mL of ε-caprolactone (manufactured by Wako Pure Chemical Industries, Ltd.), as monomers, were placed in a separable flask. Under an argon atmosphere, 0.29 g of tin(II) octylate (manufactured by Wako Pure Chemical Industries, Ltd.), as a catalyst that had been dissolved in 14.5 mL of toluene (super dehydrated) (manufactured by Wako Pure Chemical Industries, Ltd.), and 90 µL of ion exchanged water as an initiator were added to the flask, and a promoter reaction was carried out at 90° C. for one hour. Thereafter, a copolymerization reaction was allowed to proceed at 150° C. for 6 hours to obtain a crude polyhydroxyalkanoic acid B.

The thus obtained crude polyhydroxyalkanoic acid B was dissolved in 100 mL of chloroform, and the resultant added dropwise to 1,400 mL of methanol in a stirred state to obtain precipitates. The above described operation was repeated three times and, thereafter, the resulting precipitates were dried under reduced pressure at 70° C., to obtain a polyhydroxyalkanoic acid B.

A quantity of 13.4 g of the thus obtained polyhydroxyalkanoic acid B, 0.82 g of polyethylene glycol (weight average molecular weight: 10,000; manufactured by Sigma-Aldrich Inc.) having hydroxy groups at both ends, and 0.83 g of polyethylene glycol (weight average molecular weight: 10,200) having carboxyl groups at both ends were mixed. To the mixture, 0.56 g of 4,4-dimethylaminopyridinium p-toluenesulfonate (synthesized by the method described in Messmore, Benjamin W. et al., Journal of the American Chemical Society, 2004, 126, 14452), and 0.20 g of 4,4-dimethylaminopyridine (manufactured by Wako Pure Chemical Industries, Ltd.), as catalysts, were added. Under an argon atmosphere, the resulting mixture was dissolved in 28 mL of dichloromethane (dehydrated) (manufactured by Wako Pure Chemical Industries, Ltd.), and 2.06 g of dicyclohexylcarbodiimide (manufactured by Sigma-Aldrich Co.) as a condensing agent that had been dissolved in 7 mL of dichloromethane was added thereto, followed by condensation polymerization at room temperature for two days.

To the resulting reaction mixture, 60 mL of chloroform was added, and the resultant added dropwise to 1,000 mL of methanol in a stirred state to obtain precipitates. The resulting precipitates were dissolved in 100 mL of chloroform, and the resultant added dropwise to 1,000 mL of methanol in a stirred state to obtain precipitates. The above described operation was repeated twice to obtain a purified block copolymer of Reference Example 14, as precipitates.

Reference Example 15

A quantity of 10.1 g of the thus obtained polyhydroxyalkanoic acid B, 2.45 g of polyethylene glycol (weight average molecular weight: 10,000; manufactured by Sigma-Aldrich Inc.) having hydroxy groups at both ends, and 2.50 g of polyethylene glycol (weight average molecular weight: 10,200) having carboxyl groups at both ends were mixed. To the mixture, 0.56 g of 4,4-dimethylaminopyridinium p-toluenesulfonate (synthesized by the method described in Messmore, Benjamin W. et al., Journal of the American Chemical Society, 2004, 126, 14452), and 0.20 g of 4,4-dimethylaminopyridine (manufactured by Wako Pure Chemical Industries, Ltd.), as catalysts, were added. Under an argon atmosphere, the resulting mixture was dissolved in 28 mL of dichloromethane (dehydrated) (manufactured by Wako Pure Chemical Industries, Ltd.), and 2.06 g of dicyclohexylcarbodiimide (manufactured by Sigma-Aldrich Co.) as a condensing agent that had been dissolved in 7 mL of dichloromethane was added thereto, followed by condensation polymerization at room temperature for two days.

To the resulting reaction mixture, 60 mL of chloroform was added, and the resultant added dropwise to 1,000 mL of methanol in a stirred state to obtain precipitates. The resulting precipitates were dissolved in 100 mL of chloroform, and the resultant added dropwise to 1,000 mL of methanol in a stirred state to obtain precipitates. The above described operation was repeated twice to obtain a purified block copolymer of Reference Example 15 as precipitates.

Example 6

A coated cylindrical body was prepared in the same manner as in Example 1, except that the block copolymer of Reference Example 14 was used instead of the block copolymer of Reference Example 1. Specifically, the block copolymer of Reference Example 14 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Example 6.

Comparative Example 10

A coated cylindrical body was prepared in the same manner as in Example 1, except that the block copolymer of Reference Example 15 was used instead of the block copolymer of Reference Example 1. Specifically, the block copolymer of Reference Example 15 was dissolved in chloroform to prepare a solution having a concentration of 20% by weight. The resulting solution was coated on the cylindrical substrate A composed of the polyethylene terephthalate fibers to form a coating layer to obtain a coated cylindrical body of Comparative Example 10.

For each of the coated cylindrical bodies of Examples 1 to 6 and Comparative Examples 1 to 10, the elongation rate (%) of the cylindrical substrate; the value of (L2−L1)/L1; the value of (a−b)/a; the surface roughness of the inner surface (m); the ratio of the total mass of the alkylene glycol residue(s) with respect to the total mass of the block copolymer (%); the ratio of the total mass of the caprolactone residue(s) with respect to the total mass of the block copolymer (%); the ratio of the total mass of the glycolic acid residue(s) with respect to the total mass of the block copolymer (%); and the Young's modulus (MPa) of the block copolymer as measured in the form of a film; were measured and the thus measured values are shown in the following Table 4.

TABLE 4

| | Elongation rate (%) under a load of 20 N | (L2−L1)/L1 | (a−b)/a | Inner surface roughness (μm) | Ratio of total mass of alkylene glycol residue (wt %) | Ratio of total mass of caprolactone residue (wt %) | Ratio of total mass of glycolic acid residue (wt %) | Young's modulus (MP3) |
|---|---|---|---|---|---|---|---|---|
| Example 1 | 15 | 0.27 | 0.07 | 58 | 5 | 39 | 0 | 4.2 |
| Example 2 | 15 | 0.27 | 0.07 | 58 | 11 | 52 | 0 | 5.1 |
| Example 3 | 15 | 0.27 | 0.07 | 58 | 22 | 46 | 0 | 5.3 |
| Example 4 | 15 | 0.27 | 0.07 | 58 | 25 | 30 | 0 | 6.9 |
| Example 5 | 45 | 0.24 | 0.07 | 61 | 11 | 52 | 0 | 5.1 |
| Comparative Example 1 | 15 | 0.27 | 0.07 | 58 | 28 | 42 | 0 | 9.8 |
| Comparative Example 2 | 15 | 0.27 | 0.07 | 58 | 38 | 25 | 0 | 24.4 |
| Comparative Example 3 | 15 | 0.27 | 0.07 | 58 | 49 | 20 | 0 | 33.6 |
| Comparative Example 4 | 15 | 0.27 | 0.07 | 58 | 0 | 61 | 12 | 211.4 |
| Comparative Example 5 | 15 | 0.27 | 0.07 | 58 | 0 | 39 | 1 | 2.7 |
| Comparative Example 6 | 45 | 0.24 | 0.07 | 61 | 28 | 42 | 0 | 9.8 |
| Comparative Example 7 | 2 | 0.01 | 0.00 | 271 | 11 | 52 | 0 | 5.1 |
| Comparative Example 8 | 2 | 0.01 | 0.00 | 271 | 28 | 42 | 0 | 9.8 |

TABLE 4-continued

| | Elongation rate (%) under a load of 20 N | (L2−L1)/ L1 | (a−b)/a | Inner surface roughness (μm) | Ratio of total mass of alkylene glycol residue (wt %) | Ratio of total mass of caprolactone residue (wt %) | Ratio of total mass of glycolic acid residue (wt %) | Young's modulus (MP3) |
|---|---|---|---|---|---|---|---|---|
| Comparative Example 9 | 2 | 0.00 | 0.00 | 220 | 11 | 52 | 0 | 5.1 |
| Example 6 | 15 | 0.27 | 0.07 | 58 | 11 | 65 | 0 | 6.5 |
| Comparative Example 10 | 15 | 0.27 | 0.07 | 58 | 32 | 49 | 0 | 15.3 |

For each of the coated cylindrical bodies of Examples 1 to 6 and Comparative Examples 1 to 10, the kink radius (mm), the coating thickness (μm), the elongation rate (%) in a wet state, and the number of platelets adhered (%) were measured in accordance with the Measurement Examples 10 to 13. The results are shown in Table 5.

Measurement Example 10: Kink Resistance Test

A loop was formed with each of the coated cylindrical bodies of Examples 1 to 6 and Comparative Examples 4, 5 and 7 to 10, without applying an internal pressure thereto. Then a tube having a radius of R (mm) was inserted into the loop, and the diameter of the loop was gradually reduced. Thereafter, we confirmed whether the coated cylindrical body buckles or not during the period until the loop diameter reached the tube diameter, and if the coated cylindrical body did not buckle, the cylindrical body was defined as having a kink radius of R (mm) or less. The results are shown in Table 5.

Measurement Example 11: Measurement of Coating Thickness

Each of the coated cylindrical bodies of Examples 1 to 6 and Comparative Examples 1 to 10 was cut in the circumferential direction, and the thickness of the block copolymer layer in the cross section was measured by SEM. The measurement was carried out five times, in different visual fields, and the mean value of the thus measured thicknesses of the block copolymer layer was defined as the coating thickness (μm). The results are shown in Table 5.

Measurement Example 12: Evaluation of Antithrombogenicity Using Pig Platelet-Rich Plasma (Pig PRP)

A citric acid-added pig blood was centrifuged at 130 g for 15 minutes, and the supernatant collected. Saline was added to the collected supernatant to prepare a diluted PRP.

Each of the coated cylindrical bodies of Examples 1 to 6 and Comparative Examples 1 to 10 was cut such that the length in the longitudinal direction was 3 cm, and joints (manufactured by Isis) attached to both ends of the cylindrical body to be used as a test standard sample.

The test standard sample and a pump were connected by silicone tubes, and the prepared circuit filled with the diluted PRP. After circulating the diluted PRP at room temperature for 30 minutes, the test standard sample was taken off, and the length thereof measured. The elongation rate (%) in a wet state of each of the coated cylindrical bodies of Examples 1 to 6 and Comparative Examples 1 to 10 was calculated, in accordance with Formula (11). The results are shown in Table 5.

$$\text{Elongation rate (\%) in a wet state} = (D2-D1)/(D1) \times 100 \quad (11)$$

D1: length (cm) of coated cylindrical body before circulation test

D2: length (cm) of coated cylindrical body after circulation test

Subsequently, the test standard sample after the circulation test was punched by a biopsy trepan (diameter: 6 mm), and washed with PBS (−) three times.

The number of platelets adhered to the test standard sample which had been washed was calculated using an LDH Cytotoxicity Detection Kit (manufactured by Takara Bio Inc.). At this time, the number of platelets adhered to the coated cylindrical body of Example 1 was taken as 100%, and other Examples and Comparative Examples were relatively compared with respect to Example 1. The results are shown in Table 5.

TABLE 5

| | Measurement Example 10 Kink radius | Measurement Example 11 Coating thickness (μm) | Elongation rate (%) | Measurement Example 12 Number of platelets adhered (%) (with respect to Example 1) |
|---|---|---|---|---|
| Example 1 | ≤8 mm | 25 | 1.1 | 100 |
| Example 2 | ≤8 mm | 35 | 1.4 | 84 |
| Example 3 | ≤8 mm | 19 | 8.9 | 96 |
| Example 4 | ≤8 mm | 58 | 13.8 | 158 |
| Example 5 | ≤8 mm | 31 | 0.7 | 80 |
| Comparative Example 1 | Not measured | 13 | 18.6 | 263 |
| Comparative Example 2 | Not measured | 30 | 28.1 | 280 |
| Comparative Example 3 | Not measured | 66 | 31.8 | 333 |
| Comparative Example 4 | ≥15 mm | 19 | 0.0 | Not measured |
| Comparative Example 5 | ≤8 mm | 46 | 0.7 | 199 |
| Comparative Example 6 | Not measured | 28 | 15.6 | 231 |
| Comparative Example 7 | ≥15 mm | 15 | 0.0 | Not measured |
| Comparative Example 8 | ≥15 mm | 22 | 0.0 | Not measured |
| Comparative Example 9 | ≥15 mm | 19 | 0.0 | Not measured |
| Example 6 | ≤8 mm | 40 | 1.2 | 82 |
| Comparative Example 10 | ≤8 mm | 42 | 19.5 | 265 |

Measurement Example 13: Evaluation of Patency Rate in Implantation Experiment in Dogs An implantation test in dogs was carried out, using each of the coated cylindrical bodies of Examples 1, 2, 4, 5 and 6 as well as Comparative Examples 1, 6, 7, 8, 9 and 10. The implantation of each coated cylindrical body (3 cm) to the carotid artery by end-to-end anastomosis was carried out for 10 cases. Three months later, an ultrasound scan was performed to confirm whether the cylindrical bodies remained patent or not.

Specifically, aspirin and dipyridamole were administered to male Beagle dogs from two days before implantation to the day of extraction. The dogs were anesthetized by isoflurane inhalation. An incision was made in the neck to expose the carotid artery, and then 100 IU/kg of heparin was administered intravenously to systemically heparinize each dog. Blood flow was blocked, and the coated cylindrical body (3 cm) was implanted into the carotid artery by end-to-end anastomosis. Thereafter, blood flow was allowed to recover, the wound closed and dogs were awakened from the anesthesia. The number of the coated cylindrical bodies occluded was counted once a week until one month after the implantation and, thereafter, once a month until three months after implantation using an ultrasound apparatus (a digital ultrasonographic diagnosis apparatus, Noblus, manufactured by Hitachi Ltd.), to confirm the number of the coated cylindrical bodies occluded until three months after the implantation. Based on the results, the patency rate (%) was calculated in accordance with Formula (12).

$$P = Np/Na \times 100 \quad (12)$$

P: patency rate (%)
Np: the number (pieces) of coated cylindrical bodies remained patent until three months after the implantation
Na: the number (pieces) of coated cylindrical bodies implanted Generally, a long-term patency is possible if occlusion does not occur until three months after the implantation. Therefore, the period for performing the implantation experiment in dogs to evaluate the patency rate was set to three months.

The patency rate (%) of the coated cylindrical body for an implant, of each of Examples 1, 2, 4, 5 and 6 as well as Comparative Examples 1, 6, 7, 8, 9 and 10 is shown in Table 6.

TABLE 6

| Cylindrical body used for implantation | Number of cases remained patent | Patency rate P (%) |
|---|---|---|
| Example 1 | 10 | 100 |
| Example 2 | 10 | 100 |
| Example 4 | 8 | 80 |
| Example 5 | 10 | 100 |
| Comparative Example 1 | 6 | 60 |
| Comparative Example 6 | 6 | 60 |
| Comparative Example 7 | 7 | 70 |
| Comparative Example 8 | 7 | 70 |
| Comparative Example 9 | 7 | 70 |
| Example 6 | 10 | 100 |
| Comparative Example 10 | 5 | 50 |

INDUSTRIAL APPLICABILITY

Our cylindrical members can be suitably used in medical applications related to implants such as artificial blood vessels and stent grafts.

The invention claimed is:

1. A cylindrical body for an implant, comprising:
   a cylindrical substrate having an elongation rate in the longitudinal direction, as measured under a tensile load of 20 N, of from 5 to 100%; and
   a block copolymer composed of a polyalkylene glycol block(s) and a polyhydroxyalkanoic acid block(s);
   wherein the block copolymer coated on the cylindrical substrate, wherein said polyhydroxyalkanoic acid block comprises a residue selected from the group consisting of lactic acid, glycolic acid and caprolactone residues;
   wherein the ratio of the total mass of the alkylene glycol residue(s) with respect to the total mass of said block copolymer is from 5 to 25%; and
   said block copolymer has a Young's modulus as measured in the form of a film of 200 MPa or less;
   wherein upon implantation, a patency rate of at least 80% is maintained.

2. The cylindrical body according to claim 1,
   wherein said polyhydroxyalkanoic acid block comprises a caprolactone residue(s), and
   the ratio of the total mass of said caprolactone residue(s) with respect to the total mass of said block copolymer is 15 to 80%.

3. The cylindrical body according to claim 1,
   wherein said polyhydroxyalkanoic acid block comprises a glycolic acid residue(s), and
   the ratio of the total mass of said glycolic acid residue(s) with respect to the total mass of said block copolymer is 10% or less.

4. The cylindrical body according to claim 1, wherein said cylindrical substrate satisfies Formula (1):

$$(L2-L1)/L1 \geq 0.1 \quad (1)$$

wherein L1 represents a gauge length when said cylindrical substrate is compressed in the longitudinal direction thereof at a stress of 0.01 cN/dtex, said gauge length is a distance between gauge lines drawn on an outer periphery of said cylindrical substrate, spaced apart by a distance 5 times the maximum value of an outer diameter of said cylindrical substrate as measured without applying a stress to said cylindrical substrate; and
   L2 represents the gauge length when said cylindrical substrate is elongated in the longitudinal direction thereof at a stress of 0.01 cN/dtex.

5. The cylindrical body according to claim 1, wherein said cylindrical substrate satisfies Formula (2):

$$0.03 \leq (a-b)/a < 0.2 \quad (2)$$

wherein a represents the outer diameter of said cylindrical substrate as measured when said cylindrical substrate is compressed in the longitudinal direction thereof at a stress of 0.01 cN/dtex; and
   b represents the outer diameter of said cylindrical substrate as measured when said cylindrical substrate is elongated in the longitudinal direction thereof at a stress of 0.01 cN/dtex.

6. The cylindrical body according to claim 1, wherein the surface roughness of the inner surface of said cylindrical substrate is 100 μm or less.

7. An artificial blood vessel comprising the cylindrical body according to claim 1.

8. A stent graft comprising the cylindrical body according to claim 1.

* * * * *